US012708603B2

(12) United States Patent
Tägil et al.

(10) Patent No.: US 12,708,603 B2
(45) Date of Patent: Aug. 18, 2026

(54) TREATMENT APPROACH BY TARGETED DELIVERY OF BIOACTIVE MOLECULES BIO MODULATED CERAMICS

(71) Applicant: Moroxite AB, Lund (SE)

(72) Inventors: Magnus Tägil, Lund (SE); Deepak Bushan Raina, Lund (SE); Lars Åke Alvar Lidgren, Lund (SE)

(73) Assignee: Moroxite AB, Lund (SE)

( * ) Notice: Subject to any disclaimer, the term of this patent is extended or adjusted under 35 U.S.C. 154(b) by 816 days.

(21) Appl. No.: 17/050,190

(22) PCT Filed: Apr. 12, 2019

(86) PCT No.: PCT/EP2019/059427
§ 371 (c)(1),
(2) Date: Oct. 23, 2020

(87) PCT Pub. No.: WO2019/206677
PCT Pub. Date: Oct. 31, 2019

(65) Prior Publication Data

US 2021/0145749 A1 May 20, 2021

(30) Foreign Application Priority Data

Apr. 23, 2018 (EP) .................................... 18168712

(51) Int. Cl.

| | |
|---|---|
| ***A61K 9/14*** | (2006.01) |
| ***A61K 9/00*** | (2006.01) |
| ***A61K 9/51*** | (2006.01) |
| ***A61K 31/4409*** | (2006.01) |
| ***A61K 31/65*** | (2006.01) |
| ***A61K 31/7036*** | (2006.01) |
| ***A61K 31/704*** | (2006.01) |
| ***A61K 38/08*** | (2019.01) |
| ***A61K 51/12*** | (2006.01) |
| ***A61L 27/18*** | (2006.01) |
| ***A61L 27/20*** | (2006.01) |
| ***A61L 27/36*** | (2006.01) |
| ***A61L 27/46*** | (2006.01) |
| ***A61L 27/54*** | (2006.01) |
| ***A61L 27/58*** | (2006.01) |

(52) U.S. Cl.
CPC ............ *A61K 9/143* (2013.01); *A61K 9/0019* (2013.01); *A61K 9/5115* (2013.01); *A61K 31/4409* (2013.01); *A61K 31/65* (2013.01); *A61K 31/7036* (2013.01); *A61K 31/704* (2013.01); *A61K 38/08* (2013.01); *A61K 51/1244* (2013.01); *A61L 27/18* (2013.01); *A61L 27/20* (2013.01); *A61L 27/3608* (2013.01); *A61L 27/365* (2013.01); *A61L 27/46* (2013.01); *A61L 27/54* (2013.01); *A61L 27/58* (2013.01); *A61L 2400/06* (2013.01); *A61L 2400/12* (2013.01); *A61L 2430/02* (2013.01)

(58) Field of Classification Search
CPC ........ A61L 27/46; A61L 27/365; A61K 9/143
See application file for complete search history.

(56) References Cited

U.S. PATENT DOCUMENTS

| | | | |
|---|---|---|---|
| 5,716,359 A | 2/1998 | Ojima et al. | |
| 6,767,550 B1 | 7/2004 | Genin et al. | |
| 9,180,137 B2 | 11/2015 | Sandell | |
| 9,889,155 B2 | 2/2018 | Yamamoto et al. | |
| 2003/0055512 A1* | 3/2003 | Genin .................... | A61K 6/838 606/76 |
| 2005/0026864 A1* | 2/2005 | Dixon ................ | A61K 51/0497 514/47 |
| 2008/0241256 A1 | 10/2008 | Kuhn | |
| 2009/0043389 A1 | 2/2009 | Vunjak-Novakovic et al. | |
| 2014/0302145 A1 | 10/2014 | Yamamoto et al. | |
| 2017/0056559 A1 | 3/2017 | Kettenberger et al. | |
| 2018/0055969 A1 | 3/2018 | Lidgren | |
| 2022/0118157 A1 | 4/2022 | Tagil et al. | |
| 2022/0257504 A1 | 8/2022 | Tagil et al. | |
| 2022/0287972 A1 | 9/2022 | Tagil et al. | |

FOREIGN PATENT DOCUMENTS

| | | |
|---|---|---|
| CN | 104 958 766 A | 10/2015 |
| EP | 3784303 A1 | 3/2021 |
| RU | 2016123094 | 12/2017 |
| WO | WO 00/02597 A1 | 1/2000 |
| WO | WO 01/95952 A1 | 12/2001 |
| WO | WO 02/080933 | 10/2002 |
| WO | WO 02/087649 A1 | 11/2002 |
| WO | WO 2004/078223 | 9/2004 |
| WO | WO 2007/002085 A2 | 1/2007 |
| WO | WO 2007/002085 A3 | 1/2007 |
| WO | WO 2008/041909 A1 | 4/2008 |
| WO | WO 2009/011774 A2 | 1/2009 |

(Continued)

OTHER PUBLICATIONS

Motskin et al. "Hydroxyapatite nano and microparticles: Correlation of particle properties with cytotoxicity and biostability", Biomaterials, vol. 30, Issue 19, Jul. 2009, pp. 3307-3317 (Year: 2009).*

Ogawa et al. "Development of a Novel 99Tc-Chelate-Conjugated Bisphosphonate with High Affinity for Bone as a Bone Scintigraphic Agent", The Journal of Nuclear Medicine , vol. 47 , No. 12, Dec. 2006 (Year: 2006).*

Kundu et a., Doxorubicin-intercalated nano-hydroxyapatite drug-delivery system for liver cancer: An animal model, Ceramics International, vol. 39, pp. 9557-9566, 2013.

(Continued)

*Primary Examiner* — James W Rogers
(74) *Attorney, Agent, or Firm* — KNOBBE, MARTENS, OLSON & BEAR, LLP

(57) ABSTRACT

Present invention relates to a novel composition administering pharma agents using a bi-phasic recruiting moiety.

11 Claims, 29 Drawing Sheets

(56) References Cited

FOREIGN PATENT DOCUMENTS

| | | | | |
|---|---|---|---|---|
| WO | WO 2009/011774 A3 | 1/2009 | | |
| WO | WO 2013/096797 A2 | 6/2013 | | |
| WO | WO-2014032099 A1 * | 3/2014 | .......... | A61K 31/663 |
| WO | WO 2019/206677 A1 | 10/2019 | | |

OTHER PUBLICATIONS

Pignatello et al., Synthesis and Biological Evaluation of a New Polymeric Conjugate and Nanocarrier with Osteotropic Properties, Journal of Functional Biomaterials, vol. 3, pp. 79-99, 2012.

Sarkar et al., One pot synthesis of carbon dots decorated carboxymethyl cellulose-hydroxyapatite nanocomposite for drug delivery, tissue engineering and Fe3+ion sensing, Carbohydrate Polymers, vol. 181, pp. 710-718, 2018.

Extended European Search Report mailed on Feb. 4, 2022 in Application No. EP 21198730.0 in 11 pgs.

Extended European Search Report mailed on Oct. 6, 2021 in Application No. EP 21 18 0185.7 in 12 pages.

Extended European Search Report mailed on Oct. 6, 2021 in Application No. EP 21 18 0187.3 in 14 pages.

Cleemann et al., "Dose-Dependent Resorption of Allograft by rhBMP-2 Uncompensated by New Bone Formation—A Canine Study With Implants and Zoledronate", The Journal of Arthroplasty, vol. 33, pp. 1215-1221, (2018).

G "Nes et al.," Systematic and Local Zoledronic Acid Treatment with Hydroxyapatite Bone Graft: A Historical and Histomorphometric Experimental study, Experimental and Therapeutic Medicine, vol. 12, pp. 2417-2422, (2016).

Hong et al., "Local vs. Systemic Administration of Bisphosphonates in Rat Cleft Bone Graft: A Comparative Study", PLOS ONE, vol. 13, No. 1, e0190901, (2018).

Knoch et al., "The Decrease of Particle-Induced Osteolysis after a Single Dose of Bisphosphonate", Biomaterials, vol. 26, pp. 1803-1808, (2005).

Nevins et al., "A Prospective, Randomized Controlled Preclinical Trial to Evaluate Different Formulations of Biphasic Calcium Phosphate in Combination with a Hydroxyapatite Collagen Membrane to Reconstruct Deficient Alveolar Ridges", Journal of Oral Implantology, vol. 39, No. 2, 2013.

Khoury et al., "Surgical Therapy of Peri-Implant Disease: A 3-Year Follow-Up Study of Cases Treated with 3 Different Techniques of Bone Regeneration", Journal of Periodontology, vol. 72, No. 11, 2001.

Mcnally et al., "Single-stage treatment of chronic osteomyelitis with a new absorbable, gentamicin-loaded, calcium sulphate/hydroxyapatite bio composite: a prospective series of 100 cases", The Bone & Joint Journal, vol. 98-B, No. 9, 2016.

Mistry et al., "A novel, multi-barrier, drug eluting calcium sulfate/biphasic calcium phosphate biodegradable composite bone cement for treatment of experimental MRSA osteomyelitis in rabbit model", Journal of Controlled Release, Elsevier, Amsterdam, NL, vol. 239, 2016.

Raina et al., "A Biphasic Calcium Sulphate/Hydroxyapatite Carrier Containing Bon Morphogenic Protein-2 and Zoledronic Acid Generates Bone", Scientific Reports, vol. 6, No. 1, 2016.

International Search Report mailed Jul. 24, 2019 in International Application No. PCT/EP2019/059427.

Written Opinion mailed Jul. 24, 2019 in International Application No. PCT/EP2019/059427.

International Preliminary Report on Patentability dated Jul. 31, 2020 in International Application No. PCT/EP2019/059427.

Ong, et al., "Economic Burden of Revision Hip and Knee Arthroplasty in Medicare Enrollees," Clinical Orthopaedics and Related Research, No. 446, pp. 22-28, 2006.

Panchbhavi "The Use of Calcium Sulfate and Calcium Phosphate Composite Graft to Augment Screw Purchase in Osteoporotic Ankles", Foot & Ankle International/vol. 29, No. 6, Jun. 2008 (Year: 2008).

Giger et al., "Biomedical applications of bisphosphonates", Journal of Controlled Release, vol. 167, 2013, pp. 175-188.

Kok et al., Fracture strength of the proximal femur injected with a calcium sulfate/hydroxyapatite bone substitute, Clin Biomech, 63:172-178, 2019; https://www.ncbi.nlm.nih.gov/pubmed/30903873.

Schierholz et al., "Implant infections: a haven for opportunistic bacteria", Journal of Hospital Infection, 2001, vol. 49, pp. 87-93.

Stravinskas et al., A ceramic bone substitute containing gentamicin gives good outcome in trochanteric hip fractures treated with dynamic hip screw and in revision of total hip arthroplasty: a case series, BMC Muscuskeletal Disorders, 19:438, pp. 1-7, 2018; https://www.ncbi.nlm.nih.gov/pubmed/30522476.

* cited by examiner

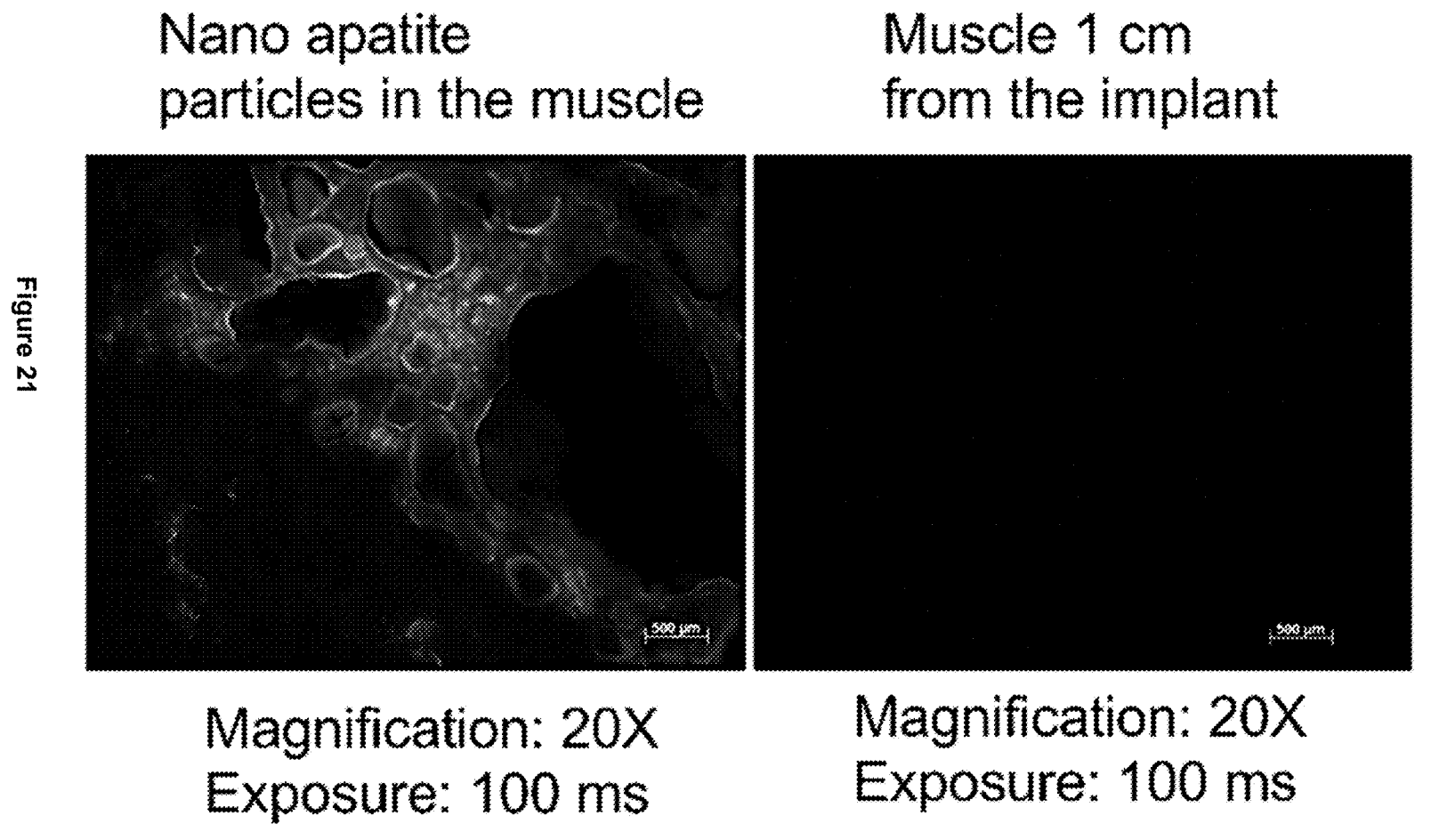

Muscle 1 cm
from the implant

500 μm

Magnification: 20X
Exposure: 100 ms

Nano apatite
particles in the muscle

500 μm

Magnification: 20X
Exposure: 100 ms

Figure 21

Doxorubicin

Rifampicin

Zoledronic Acid

Figure 22

TREATMENT APPROACH BY TARGETED DELIVERY OF BIOACTIVE MOLECULES BIO MODULATED CERAMICS

PRIORITY AND CROSS REFERENCE TO RELATED APPLICATIONS

This application is the U.S. National Stage Application under 35 U.S.C. § 371 of International Application No. PCT/EP2019/059427, filed Apr. 12, 2019, designating the U.S. and published in English as WO 2019/206677 A1 on Oct. 31, 2019, which claims the benefit of European Patent Application No. EP 18168712.0, filed Apr. 23, 2018. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

Present invention relates to an innovative method of administering one or more pharmaceutical compounds to a subject in need thereof. The invention relates to the use of a mono or biphasic material, such as e.g. a ceramic material in combination with administration of one or more pharmaceutical compounds.

BACKGROUND OF THE INVENTION

The use of ceramic material in the context of fracture healing and bone remodelling is known in the art. Treatment of larger bone defects resulting from eradication of tumours, infection or major trauma is one of the most challenging tasks in orthopaedic surgery. It often includes not only the physical filling of the defect but also aims to induce regeneration of a bone graft or bone substitute into new living bone by locally adding biologically bone active substances. Biomaterials for bone tissue engineering usually have a porous structure (micro- or macroporous), are bioresorbable, and at the same time provide sufficient structure to allow tissue formation and bone ingrowth (osteoconduction). However, biomaterials alone have not yet succeeded to induce large amounts of bone in defects. Thus, they are often combined with growth factors such as bone morphogenic proteins (BMPs) that activate bone-inducing signalling pathway. Conversely, BMPs can also lead to increased osteoclast formation and premature bone resorption, especially when used in supra physiological doses. Bisphosphonates reduce BMP-mediated bone resorption by chemically binding to hydroxyapatite (HA), which induces apoptosis in osteoclasts as these resorb and internalize the bone mineral. Zoledronic Acid (ZA) is a third-generation bisphosphonate and has been used clinically for not only systemic but also local treatment. Long-term treatment has been reported to give adverse effects so called brittle bone.

The use of ceramic materials wherein one or more pharmaceutical compounds have been absorbed or imbedded has also been employed in various compositions e.g. as injectable or pre-set compositions for controlled or extended release formulations. Examples thereof are antibiotic and cytostatic containing ceramics.

However, every new formulations have to undergo extensive preclinical and clinical testing, evaluation and documentation with respect to e.g. efficacy and safety. These procedures are time consuming and costly, and the present invention solves i.a these problems by employing known formulations in an innovative method.

Moreover, widely spread tumour with bone metastasis from mainly prostate, breast, kidney and in spread myeloma are today treated mainly with chemotherapy. Systemic osteoclast inhibitors are added in selected cases to limit local bone destruction.

In addition to focused high intensity radiotherapy from external beams, selective invasive radiation therapy (SIRT) has recently been introduced. Bone seeking radio emitters are also in early clinical use (given intravenously). Systemic side effect limits to some extent the possibilities to give a high curative dose for eradicating localized bone metastasis (that has an anatomic preference for the spine and pelvis). Beta emitters have been able to reduce pain but not improve survival. Alfa emitters reduce pain and extend survival up to approximately max 6 months depending in which stage the treatment is started.

Local direct injection or installation into a tumour with radio emitters so called brachytherapy has also been introduced especially for prostatic cancer. Radio frequency heat ablation (RFA) (heat wave) is now in limited use clinically as a mini invasive alternative to surgical eradication of tumor in the skeleton.

PMMA (Acrylate/Bone Cement) has been used the last 20 years mainly for vertebral metastasis in combination with instrumental stabilization. Also other metaphyseal and pelvic locations have been treated with PMMA. The combination of RFA prior to cement augmentation has the theoretical advantage of reducing the spread of tumor cells caused by extravasations when the cement is used.

Hydroxyapatite particles have shown a minor cytotoxic effect on bone tumour cells and with a positive response (conductive) to normal bone cells. The addition of higher dose of Zoledronic acid may give a clear but limited cytostatic effect based on the strong and lasting binding to apatite. Lower dose of ZA could have a reversed and an anabolic effect. There are approved bisphosphonate coupled with radioemitters. Ferromagnetic nanoparticles for localized chemotherapy are studied at the moment. (Tumour Magnet Therapy). New Mabs (monoclonal antibodies) are on its way, recently in metastatic melanoma and lung cancer. There are companies today that inject plain calcium sulfate with cytostatic in prostate cancer in patients with an ASA class making additional major surgery risky. This effect is however short term as the sulphate is degraded within months. Even more compelling is of course to use an apatite bone substitute as a cytostatic drug carrier and combine it with a radio emitter. In high doses, systemic tumour treatment has significant side effects and giving local treatment is a possibility if a metastasis is targeted at surgery. Very high concentrations could then be achieved without systemic side effects. There are several drug candidates that could be used for this purpose.

Musculoskeletal infections place an additional burden on the total health-care expenditures, which are rising faster than the gross domestic product in the United States 0.5-1 percent (up to 4 percent) of all primary joint implants get infected and is slightly on the rise and is 3 times higher for revision surgery Kurtz et al. used the U.S. Nationwide Inpatient Sample (1990-2003) to demonstrate that the number of infections after revision total hip arthroplasty is projected to increase from 3400 in 2005 to 46,000 in 2030, while infections after revision total knee arthroplasty are projected to increase from 6400 in 2005 to 175,500 in 2030 (Kurtz et al 2006). The total direct medical costs associated with revision total hip arthroplasty because of infection are 2.8 times higher than those associated with revision because of aseptic loosening and 4.8 times higher than the direct medical costs associated with a primary total hip arthroplasty. Peri-prosthetic infections may also become lethal with an overall mortality rate reported to range from 1% to 2.7% for patients around sixty-five years of age and increasing to 7% for patients who are more than eighty-five years old.

In prior art, first stage the implant is being removed and PMMA spacer or beds with antibiotics are being inserted for 6-12 weeks. In a second stage a cemented implant with a special PMMA with antibiotics is often used. If both bone augmentation and infection eradication could be expected in a one stage non cemented procedure this would be cost effective. If a non-cemented prosthesis is used in the second stage no local treatment is used today and here an antibiotic bone material fills a gap. If an antibiotic could be used systemically and by accretion to apatite act synergistically with a locally preloaded ceramic carrier containing a different antibiotics this could significantly reduce the risk of reoccurrence. Present invention addresses numerous of the above mentioned problems.

SUMMARY OF THE INVENTION

Present invention relates to the use of a material, such as e.g. a ceramic bio-absorbable material that may consist of one or more materials, such as e.g. a biphasic or triphasic material. The material may suitable be preset or injectable, i.e. such that the material may be administered to a subject through a tube or cannula of any kind. Alternatively, the material may be dispersed on a surface of any kind, e.g. adhered to the surface of an implantable medical device.

The material may in principle be any material or combination of various materials forming different phases. One such non-limiting example is any kind of bone substitute material which may suitable be hydroxyapatite (HA). Such material may be used alone or in combination with further components such as e.g. calcium sulphate (either as a hemi-hydrate and/or di-hydrate), collagen, alginate, cellulose, poly-lactic acid etc. i.e. polymers of natural or synthetic origin. The important feature with the material is that it has to be finely divided into micro or nanoparticles so as to provide a very large effective surface. This may be suitable achieved by any suitable technique known in the art in order to create small particles such as e.g. grinding etc. As mentioned herein, such finely divided particles may be used without addition of further materials, or may be dispersed in a second or third material. The particles dispersed or mixed with a second or more material, wherein the second or more materials are partly or totally bioabsorbable. Consequently, the material according to the invention comprises at least one first component that is not bioresorbable or very slowly bioresorable. This material may optionally comprise at least one second material that is bioresorbable at a higher rate than the first material.

The invention also relates to the use of one or more pharmaceutically active compounds. The pharmaceutical compound may in principle be any suitable compound for the condition or disease to be treated. Non-limiting examples are antibiotics, anticancer drugs, or any drugs used in any bone related disease or condition.

In one aspect, the invention relates to a method of treating a subject. The method comprises the steps of:

i) administering to a subject in need thereof at least a first finely divided (particulate) material, which may optionally comprise at least a second material, wherein the first material is not bioresorbable or very slowly bioresorbable and the second material or materials are bioresorbable at a higher rate than the first material,
ii) allowing a certain period of time to pass in order to provide for the first particulate material to be exposed to the body and/or second material or materials to be wholly or partly absorbed by the body of the subject,
iii) administering to the subject one or more pharmaceutically active compounds.

In one aspect of the invention, the administration in i) may optionally comprise a third material that is non resorbable but may act as a carrier for the first material and/or the second material.

In a further aspect, the invention relates to use of at least a first finely divided (particulate) material, which may optionally comprise at least a second material, wherein the first material is not bioresorbable or very slowly bioresorbable and the second material or materials are bioresorbable at a higher rate than the first material and one or more pharmaceutically active compounds, wherein i) at least a first finely divided (particulate) material, which may optionally comprise at least a second material, wherein the first material is not bioresorbable or very slowly bioresorbable and the second material or materials are bioresorbable at a higher rate than the first material is administered to a subject in need thereof,
ii) allowing a certain period of time to pass in order to provide for the first particulate material to be exposed to the body and/or the at least second material or materials to be wholly or partly absorbed by the body of the subject,
iii) administering to the subject one or more pharmaceutically active compounds.

In one aspect of the invention, the use in i) may optionally comprise a third material that is non resorbable but may act as a carrier for the first material and/or the second material.

Among the many problems solved by present invention, it has been observed that one of the advantages of present invention is i.a. that also using an antibiotic containing HA/S as carrier for tumour drugs in bone in combination with tumor eradication and local antibiotic release thereby prevent infection which is more common in malignancy.

The possibility then to administer at one or more occasions an additional approved antibiotic or systemic tumour agent if it could be proven that it binds with a hydroxyl apatite carrier inserted in the tumour that already may contain a cytostatic is compelling and is novel.

The inventors have shown that HA retains and release a pharma agent over an extended period (3 months Rifampicin) and retain the substance even at 6 months (with zoledronic acid). This is very different compared to prior art methods with sulphates, which releases a pharmaceutical agent for a few months.

Figure 3:
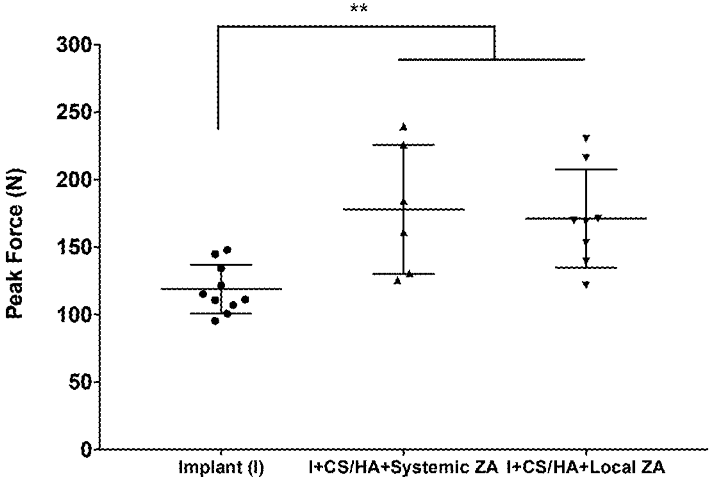
Figure 3:
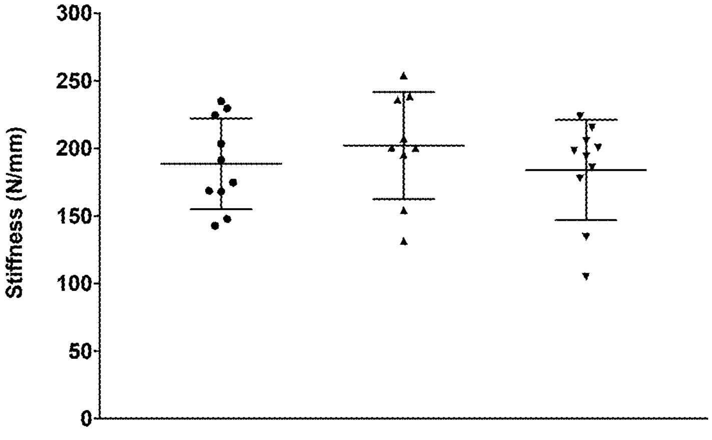
Figure 3:
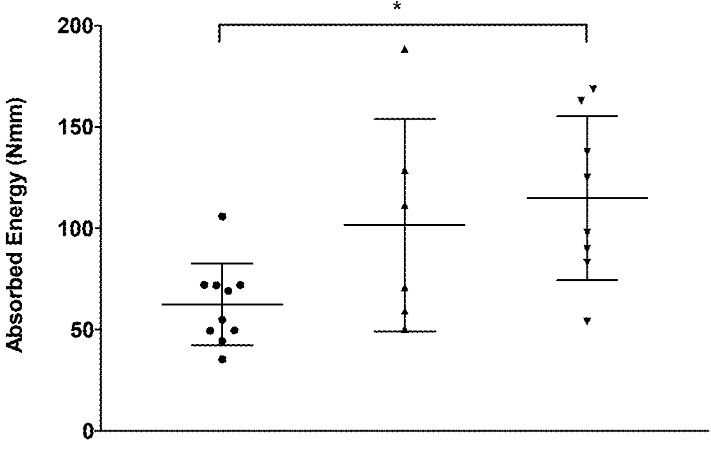

FIG. 3 illustrates results from the pull-out testing of the tibia implant. Statistically significant peak force to pull-out the implant from the tibia was observed in groups G2 (systemic ZA) and G3 (local ZA) when compared to the only implant group G1 ($p<0.01$) (FIG. 3). No differences in the stiffness were seen. Absorbed energy was significantly higher in the local ZA group (G3) when compared to the only implant group (G1) ($p<0.05$).

Figure 4:
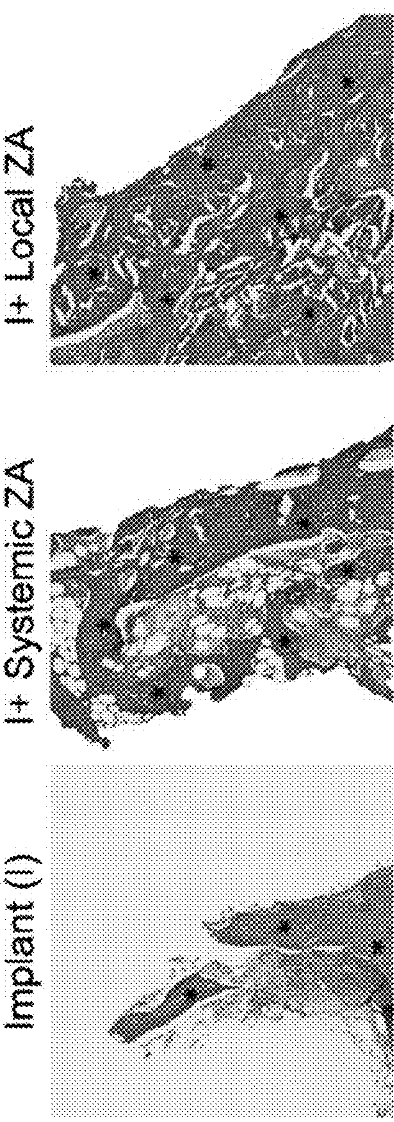

FIG. 4 illustrates histology images from the tibia implant model. * verifies bone tissue. Images are taken at 40× magnification and the images are taken of the bone formed close to the implant.

Figure 5:
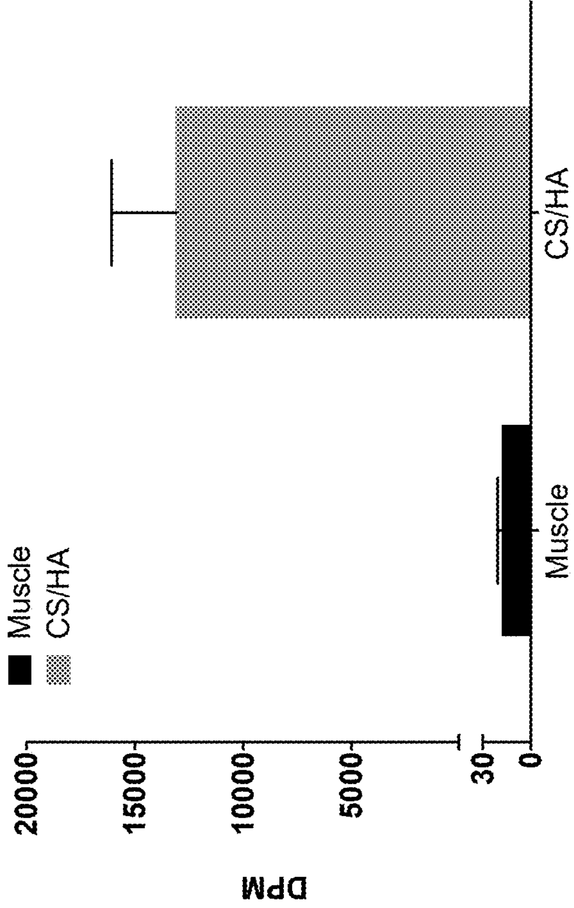

FIG. 5 illustrates uptake of $^{14}$C-ZA in the CaS/HA biomaterial placed in the ectopic muscle pouch model and the comparison of the radioactive counts with the surrounding muscle, verifying that radioactive ZA seeks the apatite-based biomaterial outside bone and verifies the findings from the bone implant model in Example 1.

Figure 6:
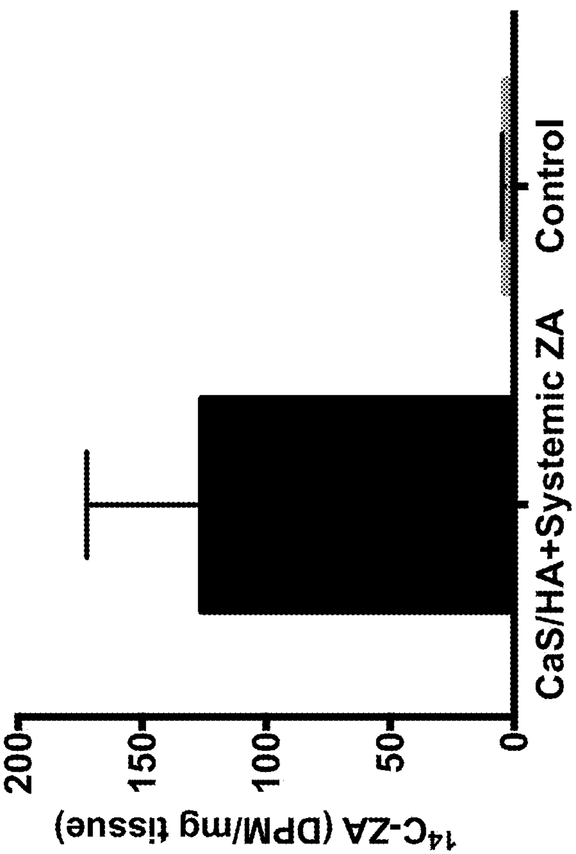

FIG. 6 illustrates uptake of $^{14}$C-ZA in the CaS/HA biomaterial placed in the femoral neck canal of osteoporotic rats, 6-months post implantation, confirming that $^{14}$C-ZA seeks and stays in the apatite material for at least 6-months post injection.

Figure 7:
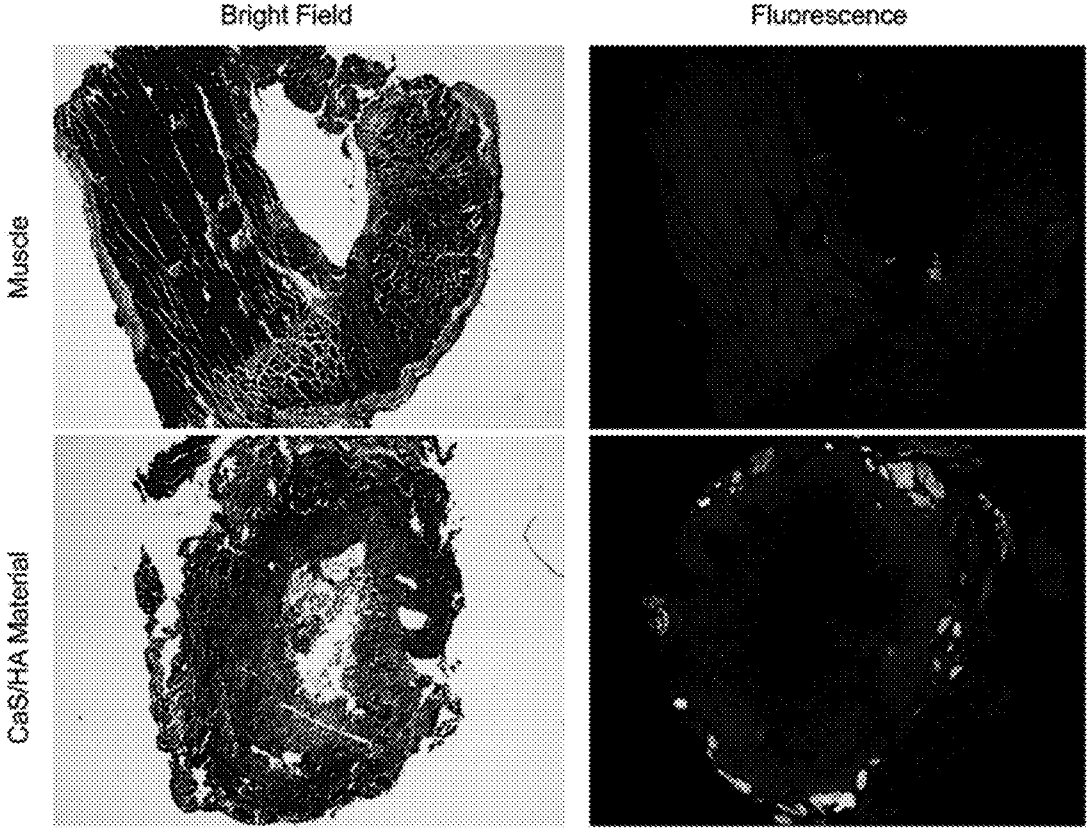

FIG. 7 illustrates uptake of tetracycline in the CaS/HA biomaterial placed in the abdominal muscle pouch model. The absence of signal from the adjacent muscle is noticeable.

Figure 8:
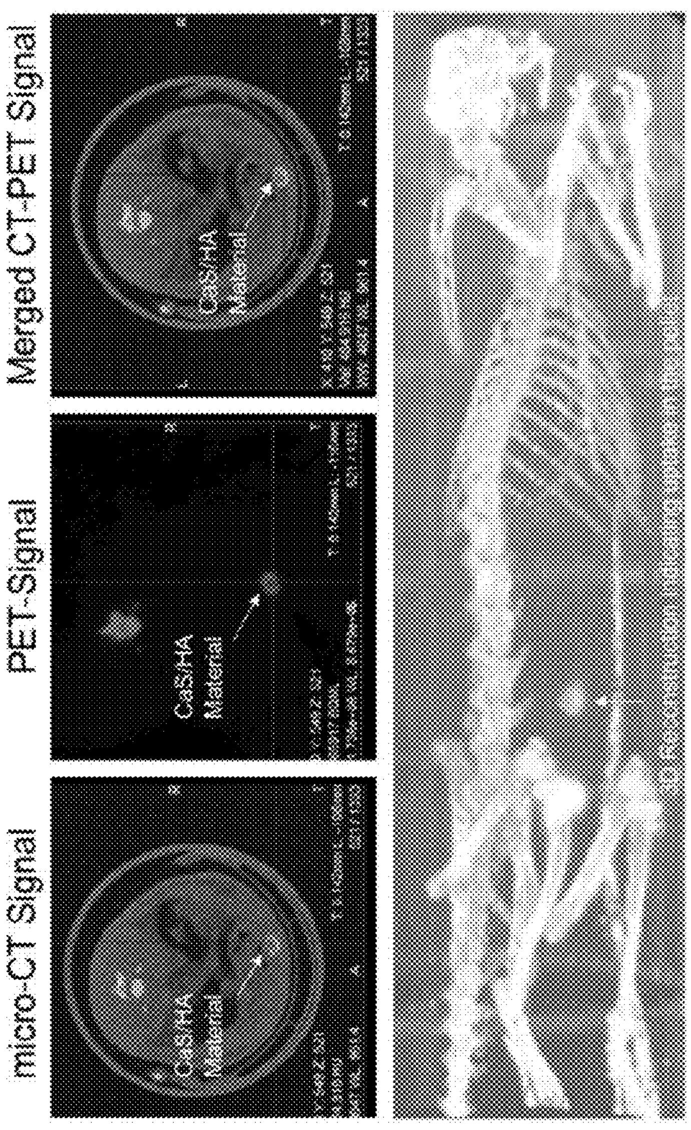

FIG. 8 illustrates micro-CT and PET based evaluation of the uptake of 18F-Fluoride tracer in the CaS/HA biomaterial placed in the abdominal muscle pouch model, 2-weeks post implantation. Top 3 panels show a plain CT image used to identify the pellet in the muscle pouch, the PET image of the same slice indicating uptake of the tracer and an overlap of the CT and PET image confirming the source of the signal (CaS/HA) material, respectively.

Figure 9:
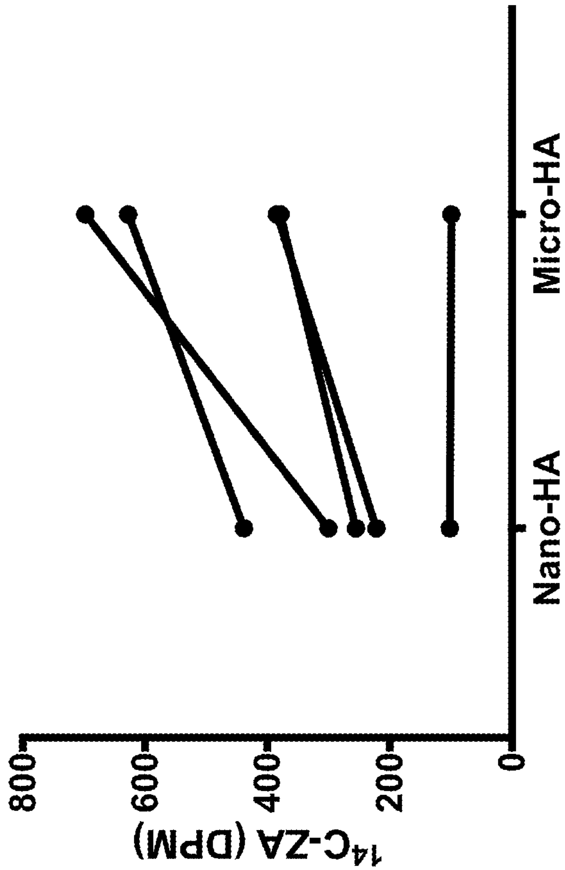

FIG. 9 illustrates data indicating apatite size dependence of drug uptake.

Figure 10:
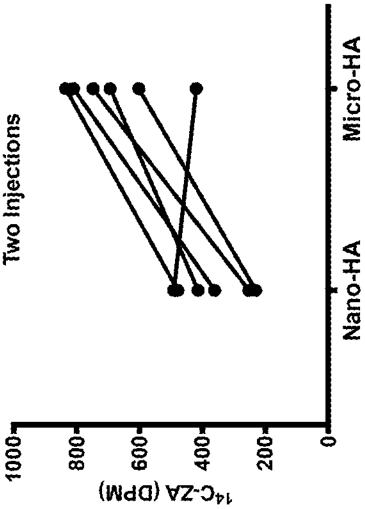
Figure 10:
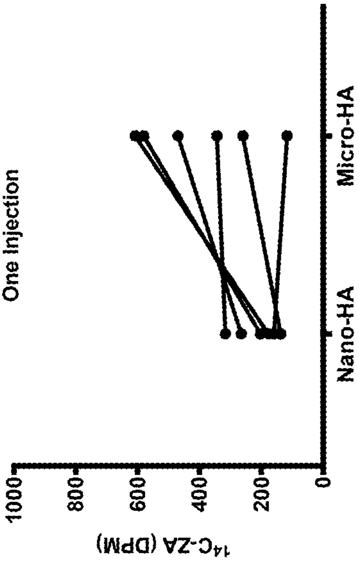

FIG. 10 illustrates the possibility of re-loading apatite particles with model drug, zoledronic acid by repeated administration of the drug.

Figure 11:
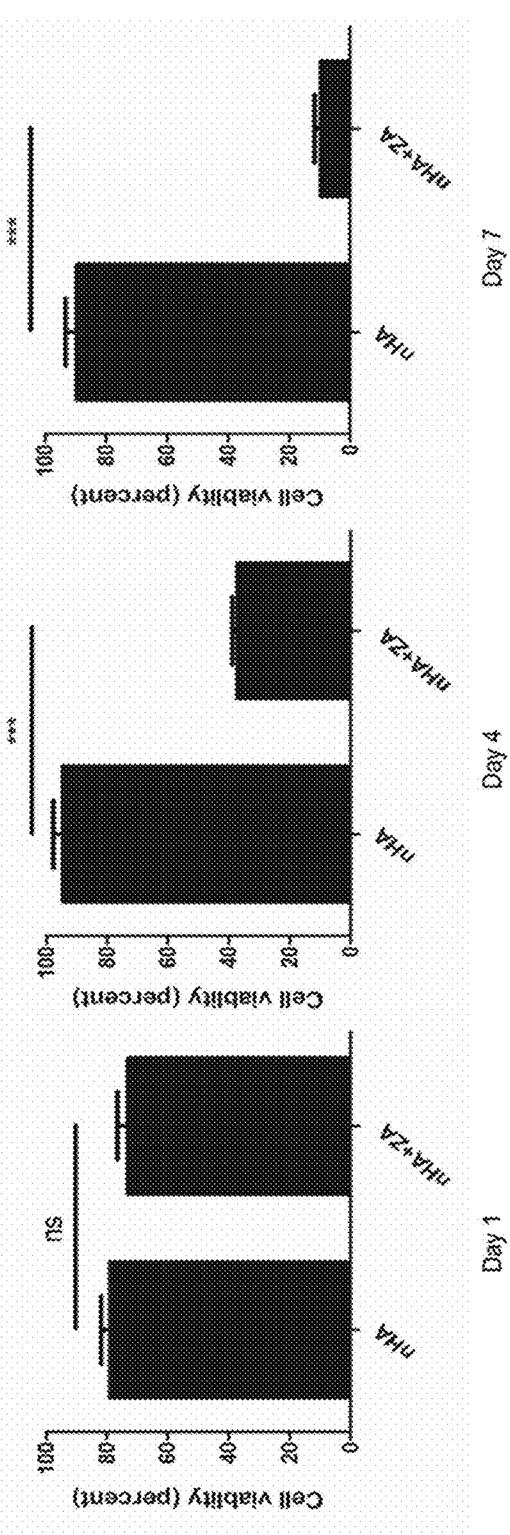

FIG. 11 illustrates results from in-vivo cytotoxicity experiment using nano apatite particles and nano apatite particles coupled with ZA (zoledronic acid).

Figure 12:
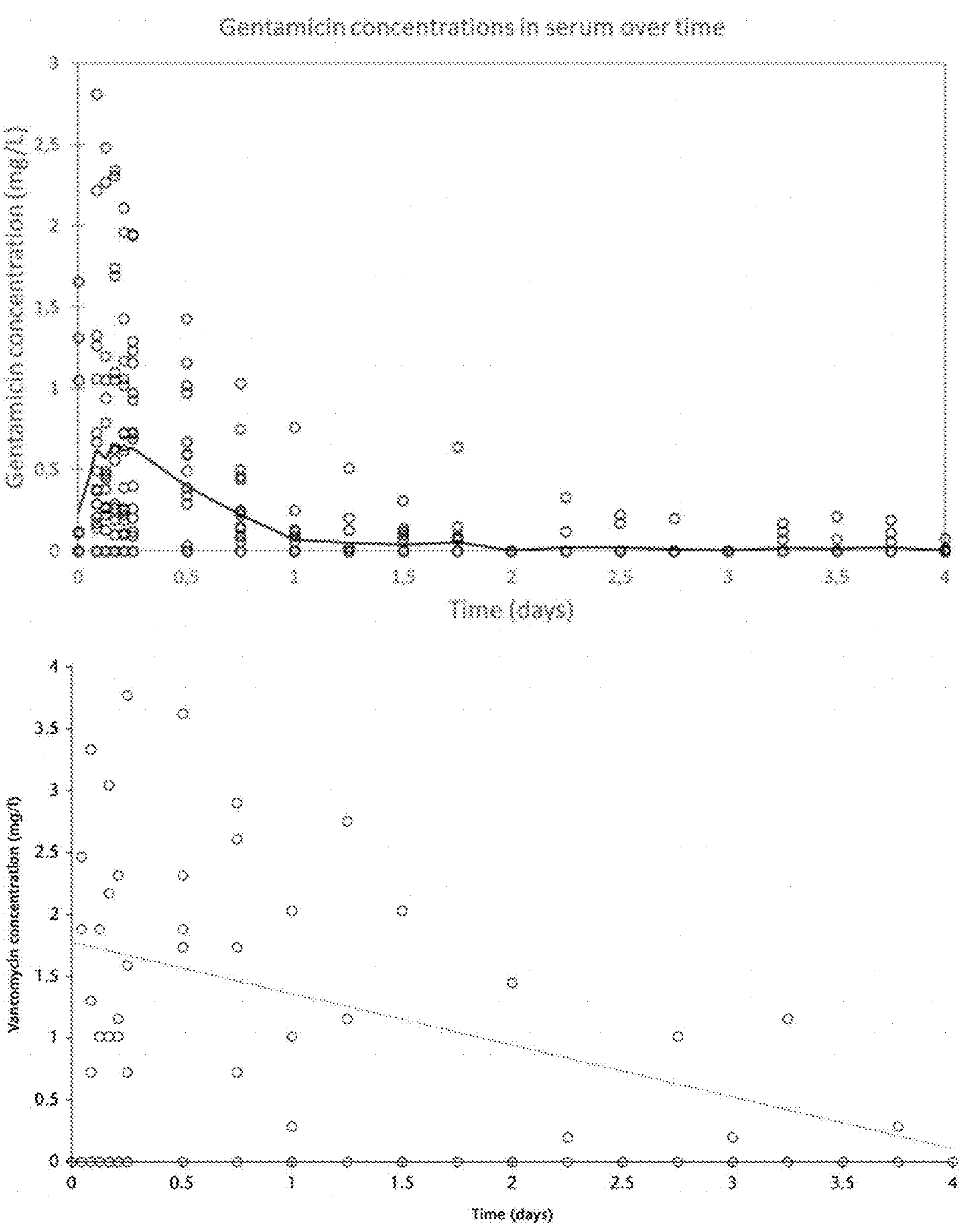

FIG. 12 illustrates in-vivo release of non-binding antibiotic gentamycin (top) and vancomycin (bottom) from a CaS/HA biomaterial from human patients.

Figure 13:
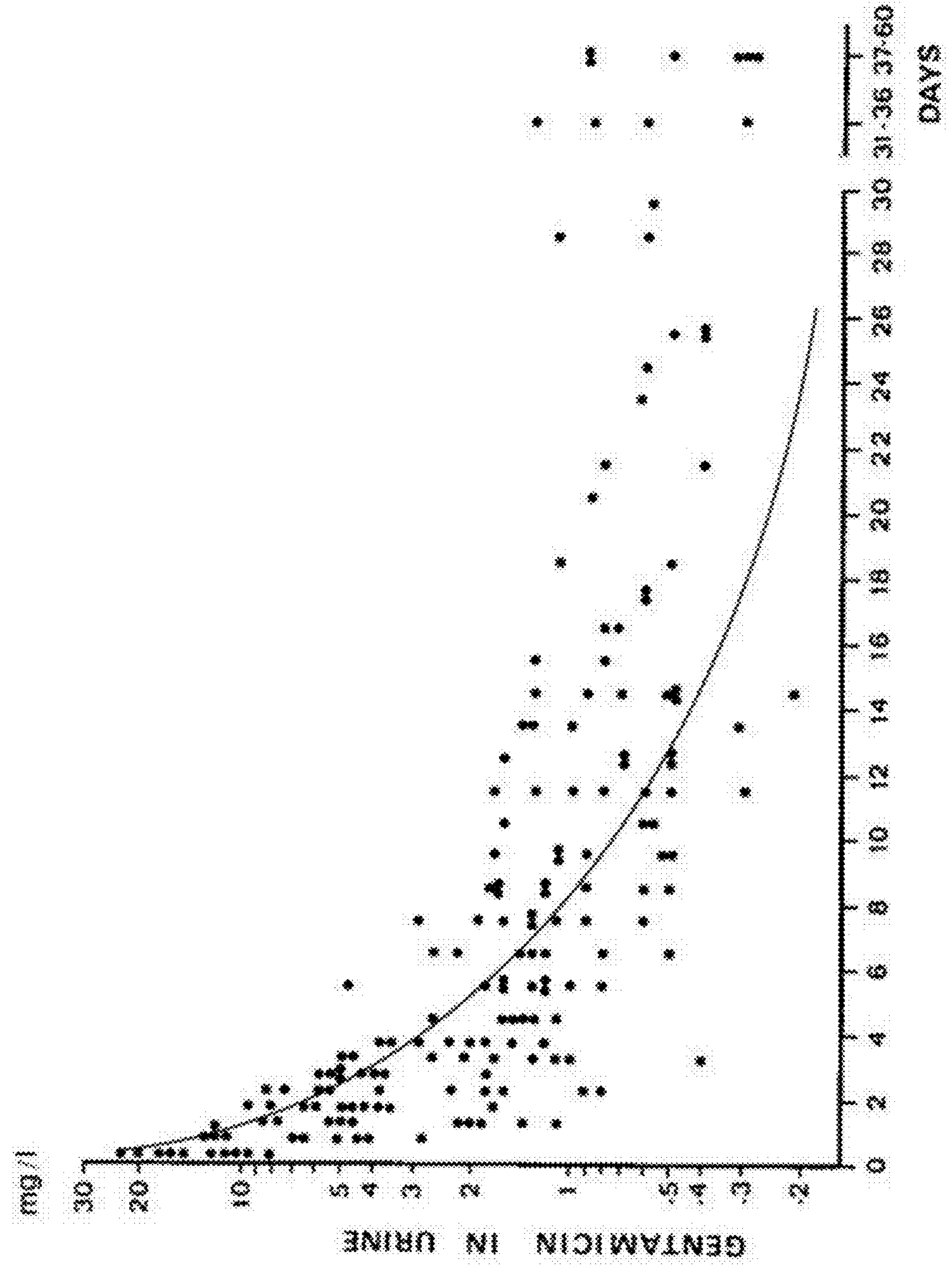

FIG. 13 illustrates long term elution of gentamycin over a period of 2-months. Comparison with PMMA containing Gentamycin. The trend line shows that the Apatite/Sulphate material releases gentamycin by 4 weeks.

Figure 14:
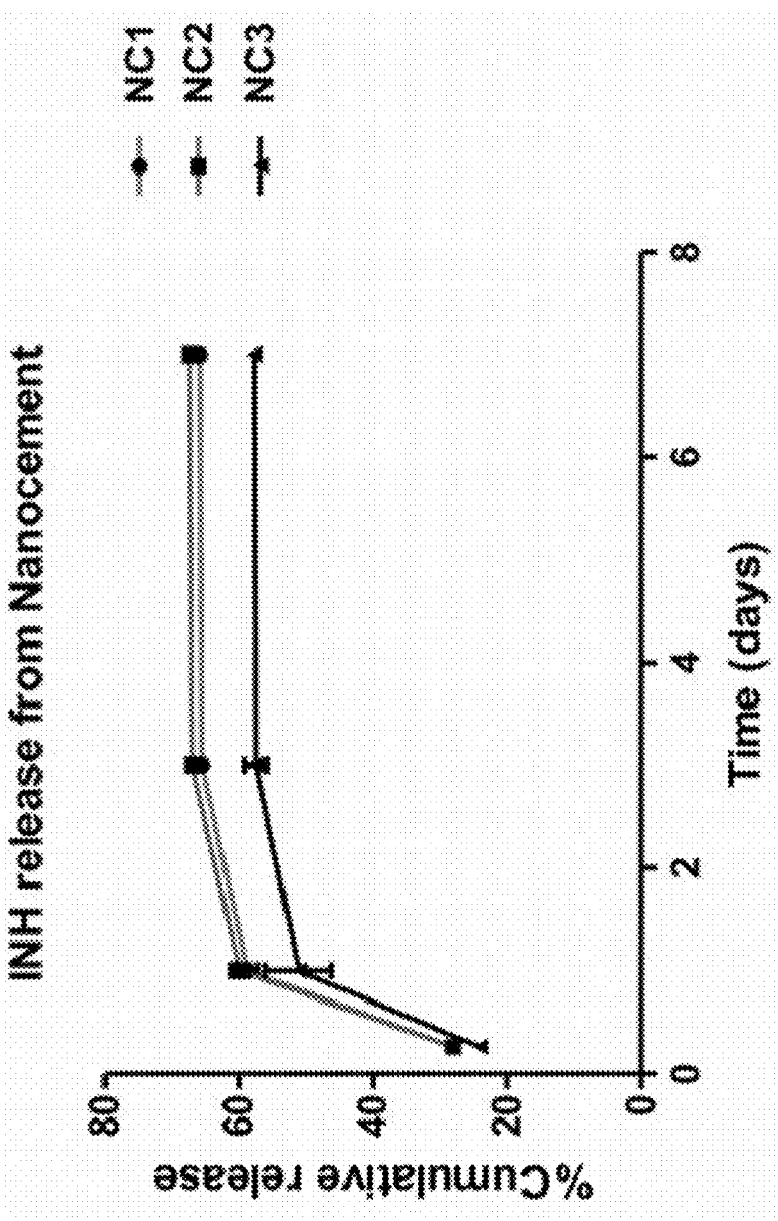

FIG. 14 illustrates in-vitro release of Isoniazid from CaS/HA biomaterial

Figure 15:
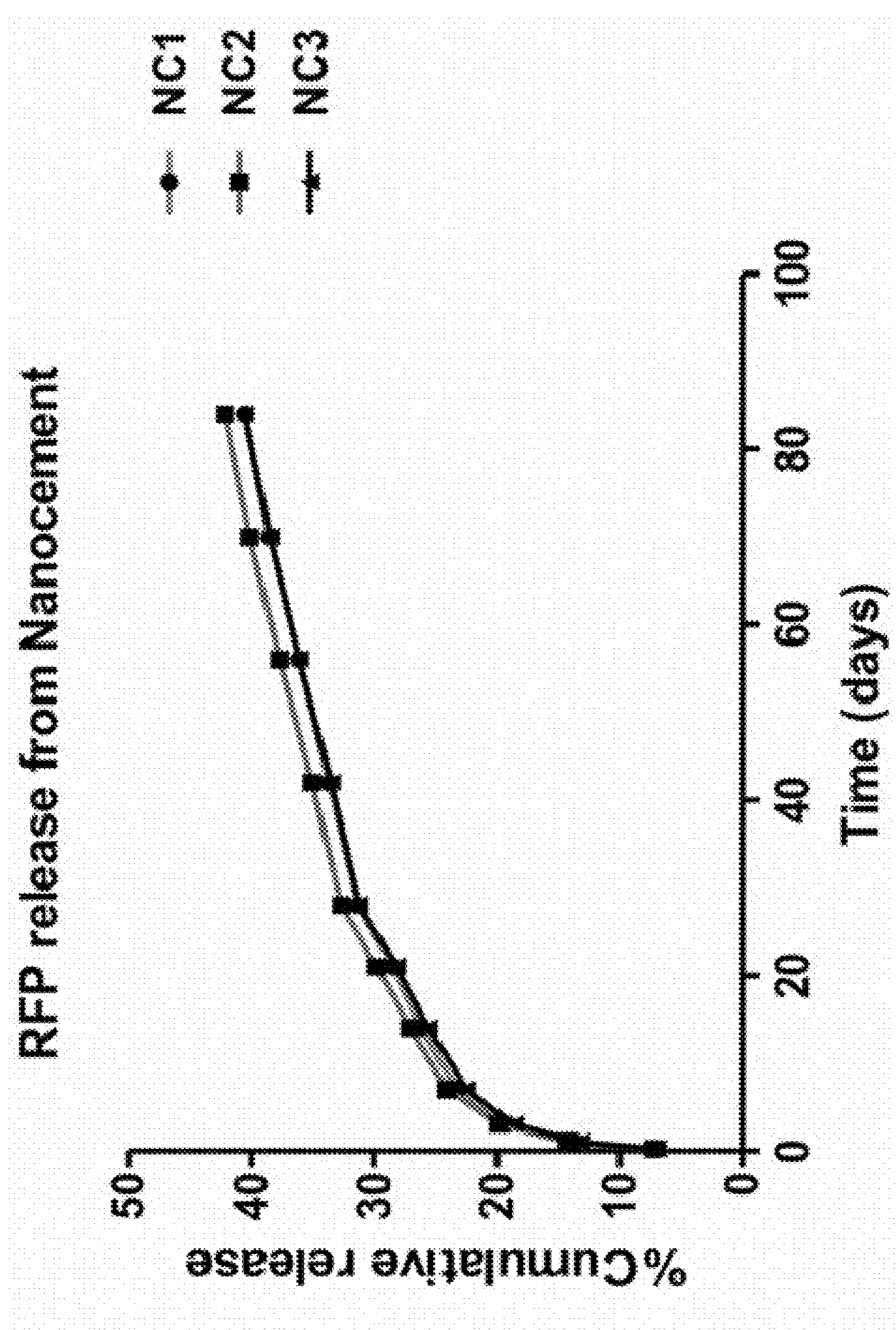

FIG. 15 illustrates in-vitro release of antibiotic rifampicin from the CaS/HA biomaterial over a period of 12-weeks.

Figure 16:
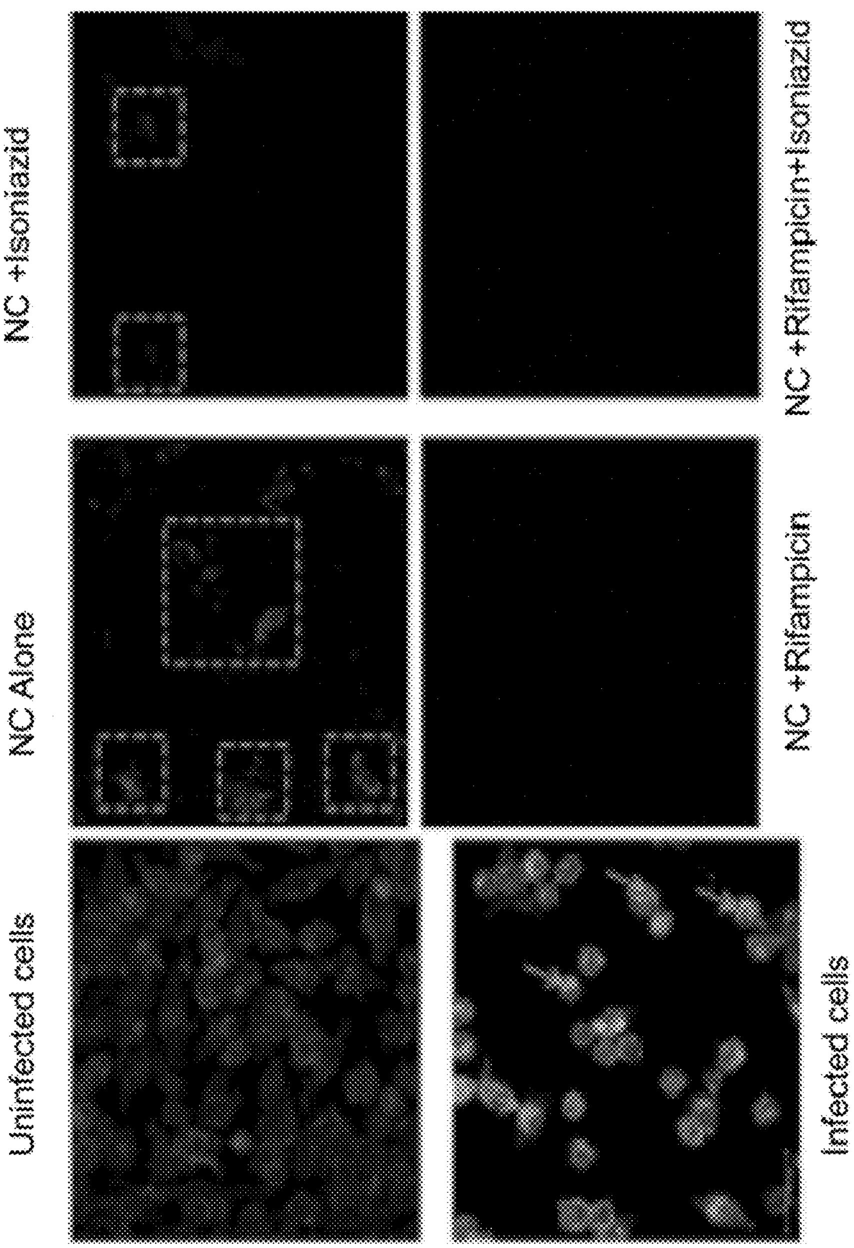
Figure 17:
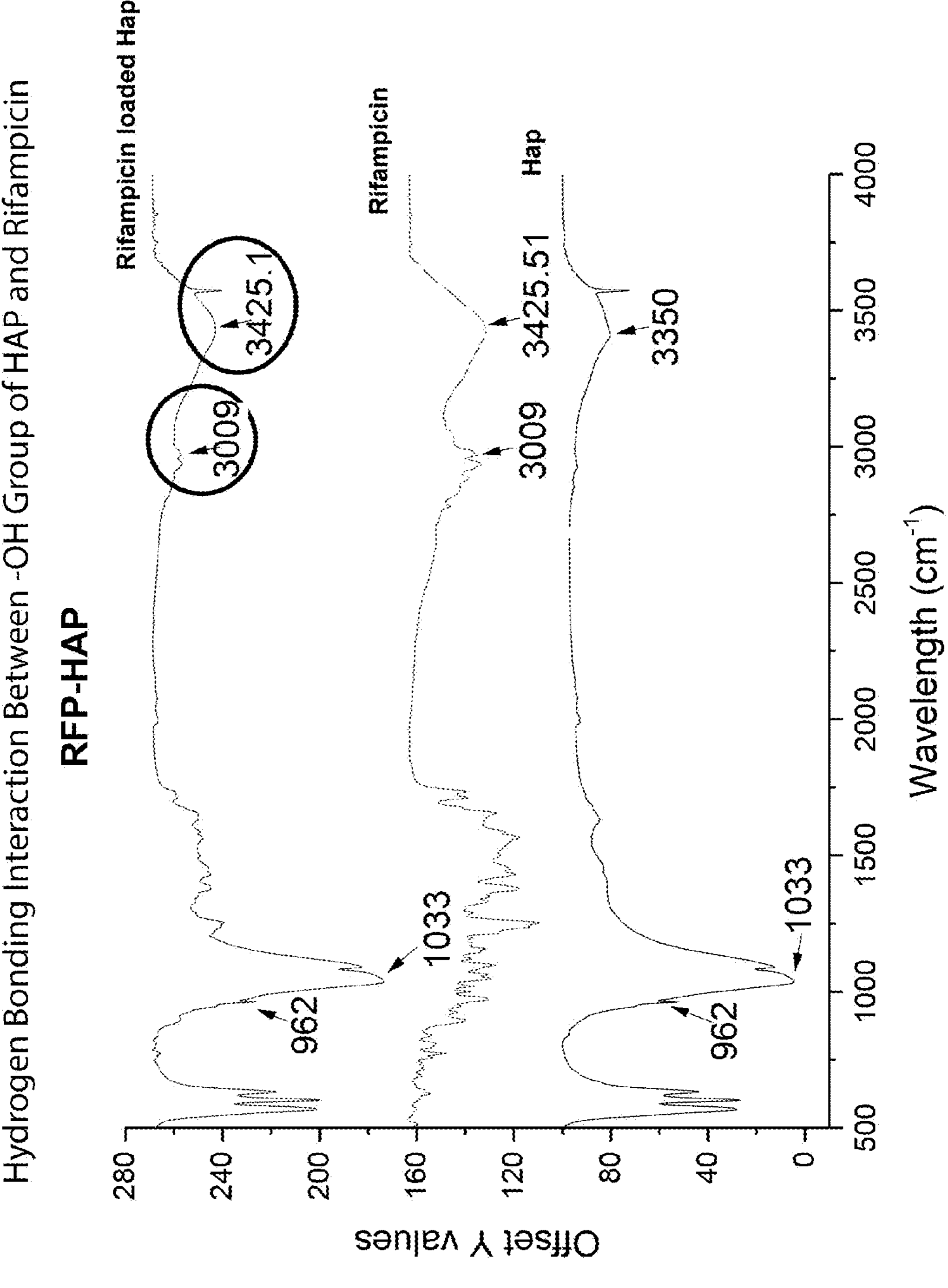

FIG. 16 illustrates fluorescent microscopy images of macrophages alone or infected with GFP expressing bacteriae. Notice the complete depletion of fluorescent signal in presence of rifampicin or the combination of rifampicin with isoniazid FIG. 17 illustrates the Fourier transform infrared (FTIR) spectra of CaS/HA material alone, rifampicin alone or the combination of rifampicin with CaS/HA showing the hydrogen bonding interaction between hydroxyl groups of apatite and rifampicin.

Figure 18:
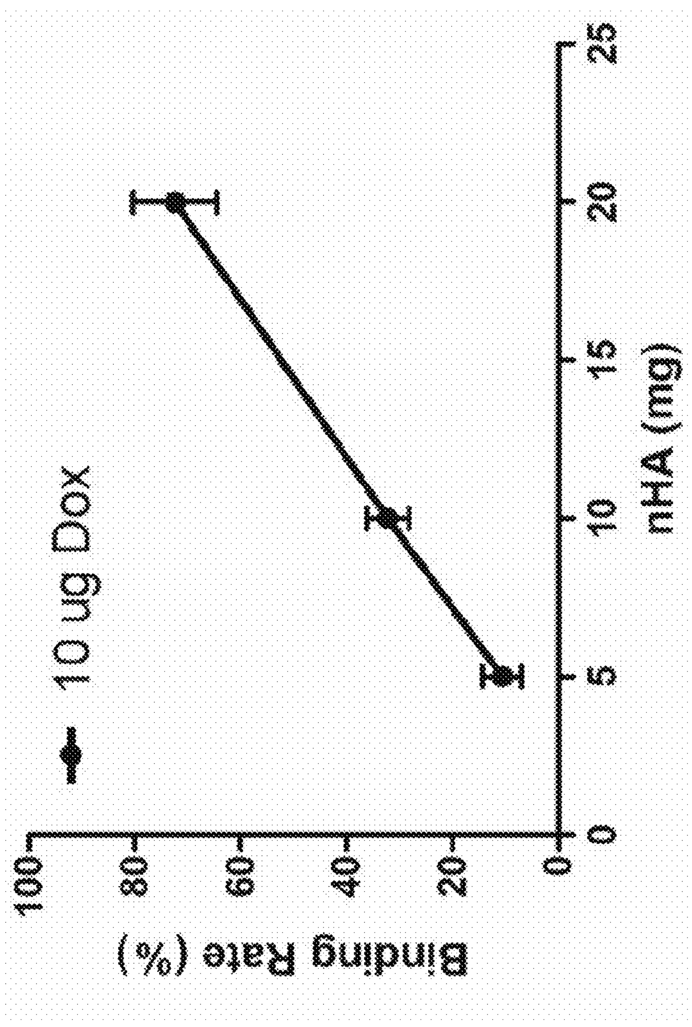

FIG. 18 illustrates hydroxyapatite particle concentration dependent binding of doxorubicin to apatite particles.

Figure 19:
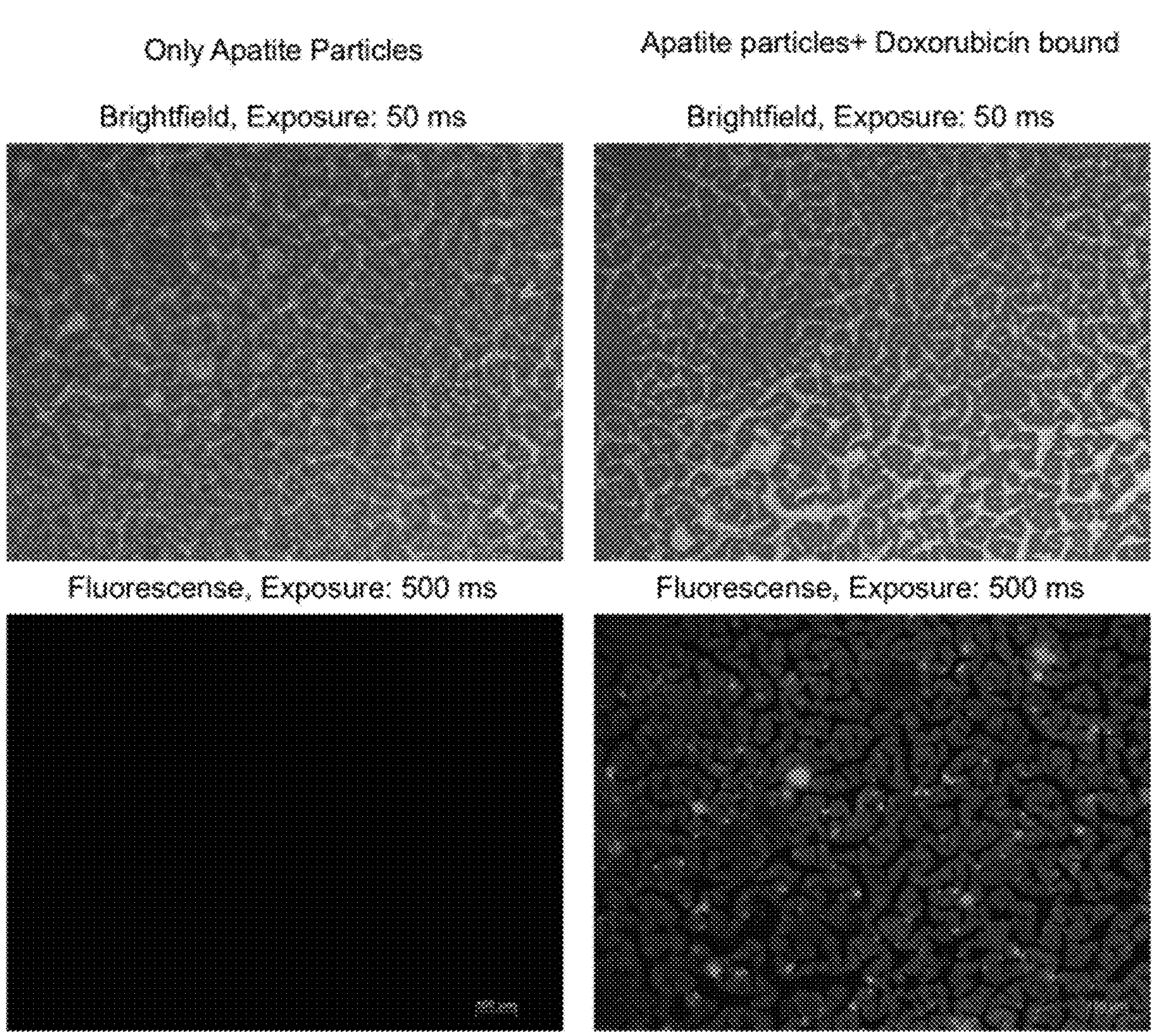

FIG. 19 illustrates fluorescence microscopy images confirming the binding of doxorubicin to apatite particles.

Figure 20:
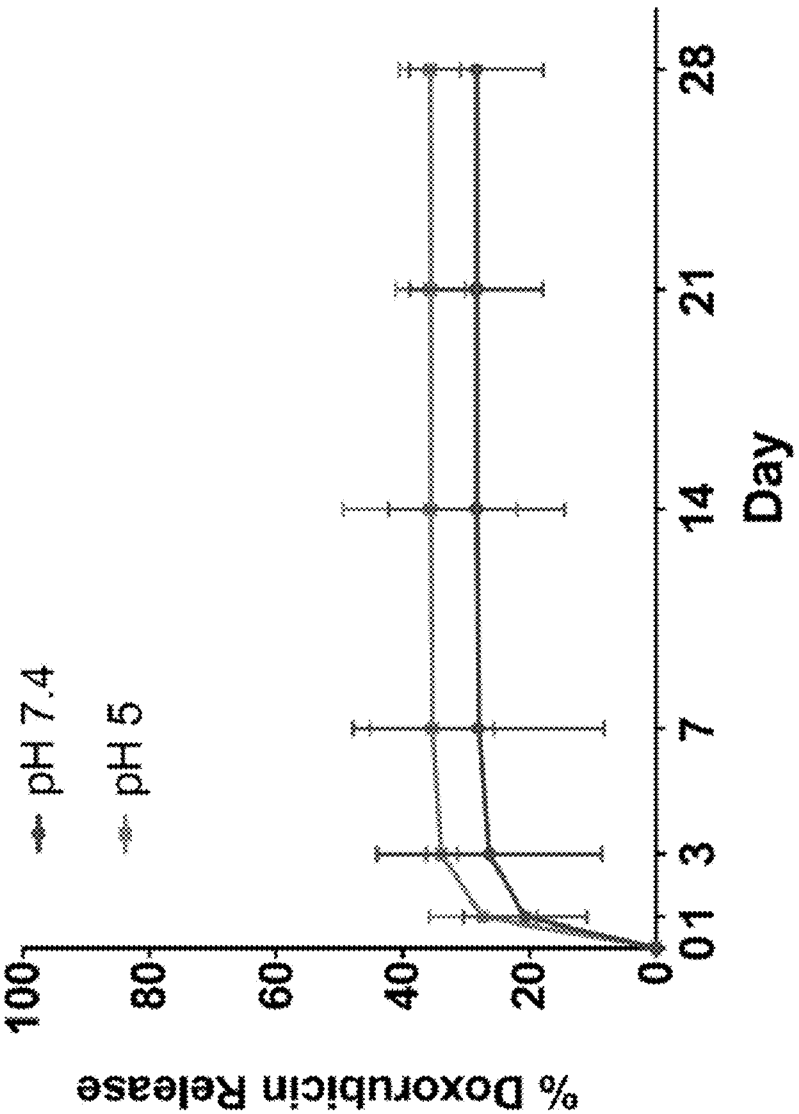

FIG. 20 illustrates in-vitro release of doxorubicin from CaS/HA biomaterial over a 4-week period.

FIG. 21 illustrates results from in-vivo doxorubicin binding to apatite particles implanted in the abdominal muscle pouch 2-weeks post implantation and analyzed using fluorescent microscopy.

Figure 22:
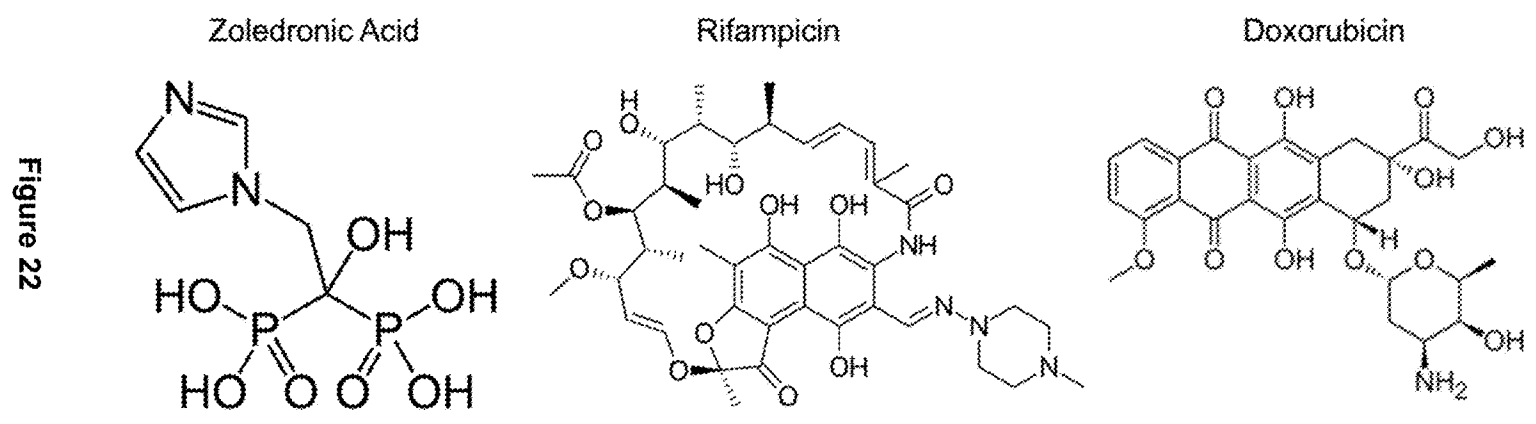

FIG. 22 illustrates the structure of the studied agents zoledronic acid, rifampicin and doxorubicin and the free hydroxyl groups in their chemical structure.

Figure 23:
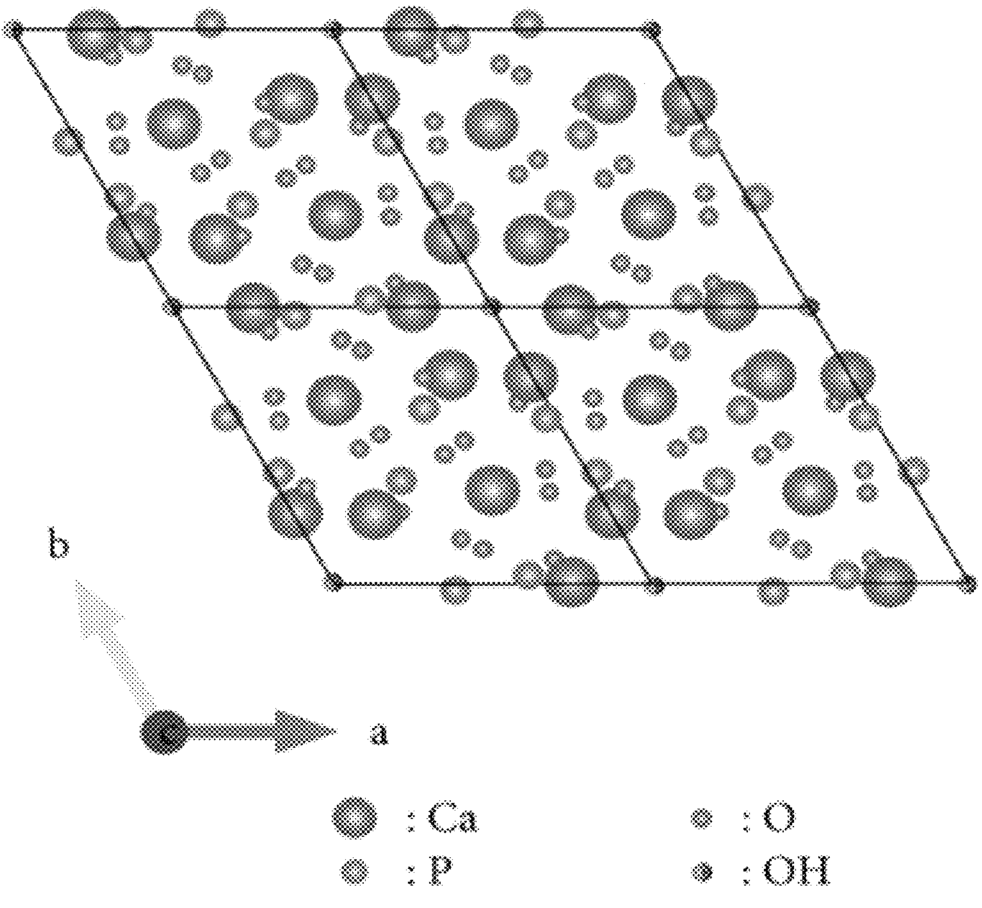

FIG. 23 illustrates the crystal structure of hydroxyapatite with possible binding sites on the lattice.

Figure 24:
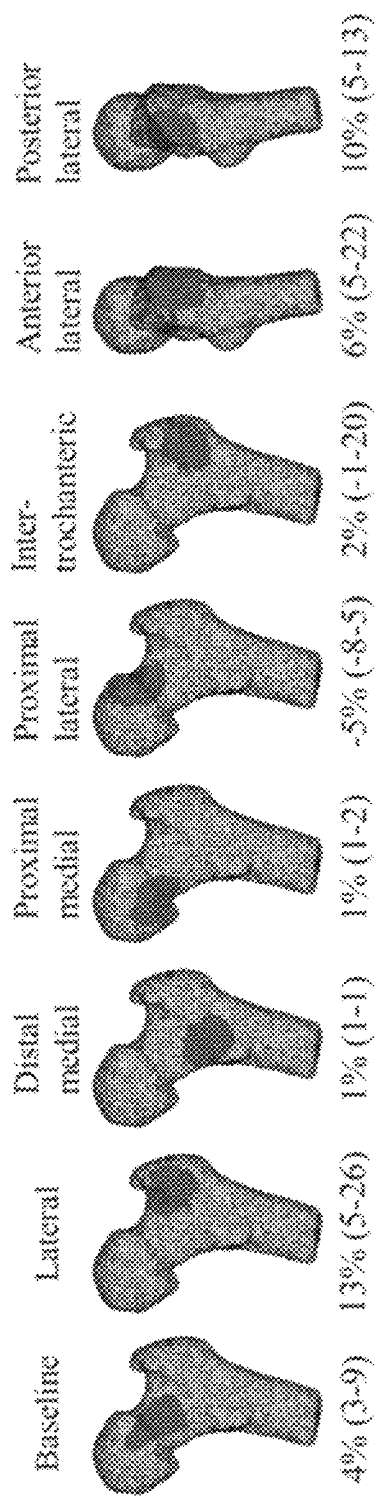

FIG. 24 illustrates the finite element modelling simulations indicating the effect of site of injecting the CaS/HA biomaterial on increase in strength (indicated in brackets).

Figure 25:
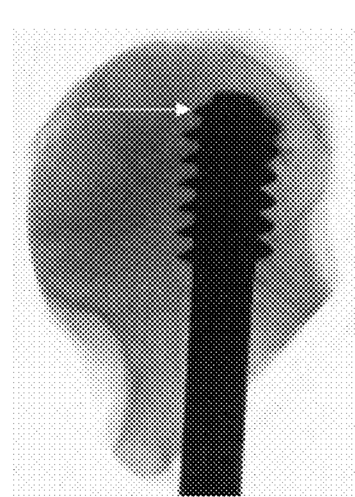
Figure 25:
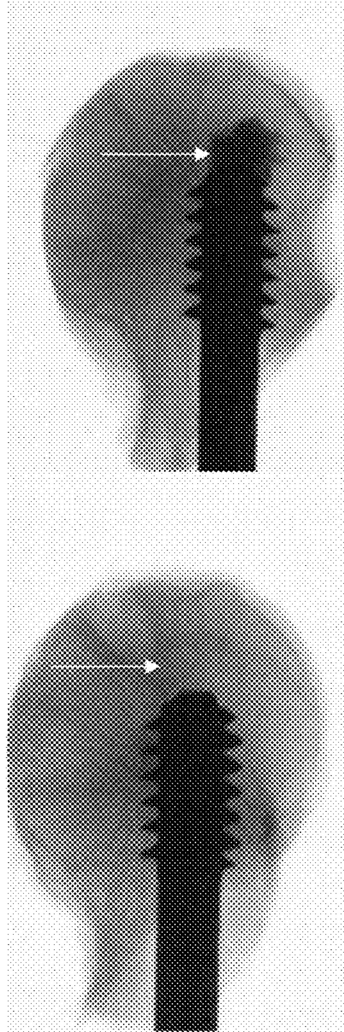

FIG. 25 illustrates a method for injecting the CaS/HA biomaterial into the femoral head of human specimens.

Figure 26:
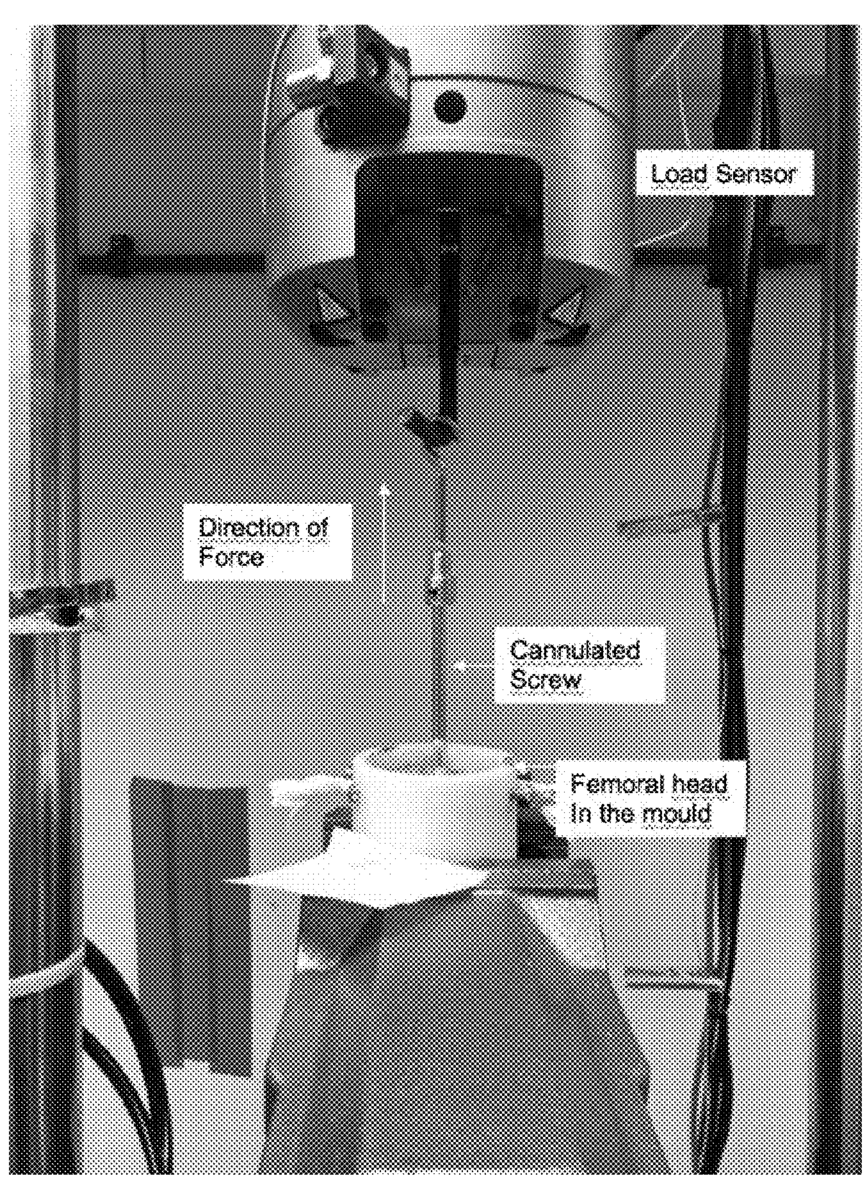

FIG. 26 illustrates the set-up used for the pull-out testing of the cannulated screw from human femoral heads.

Figure 27:
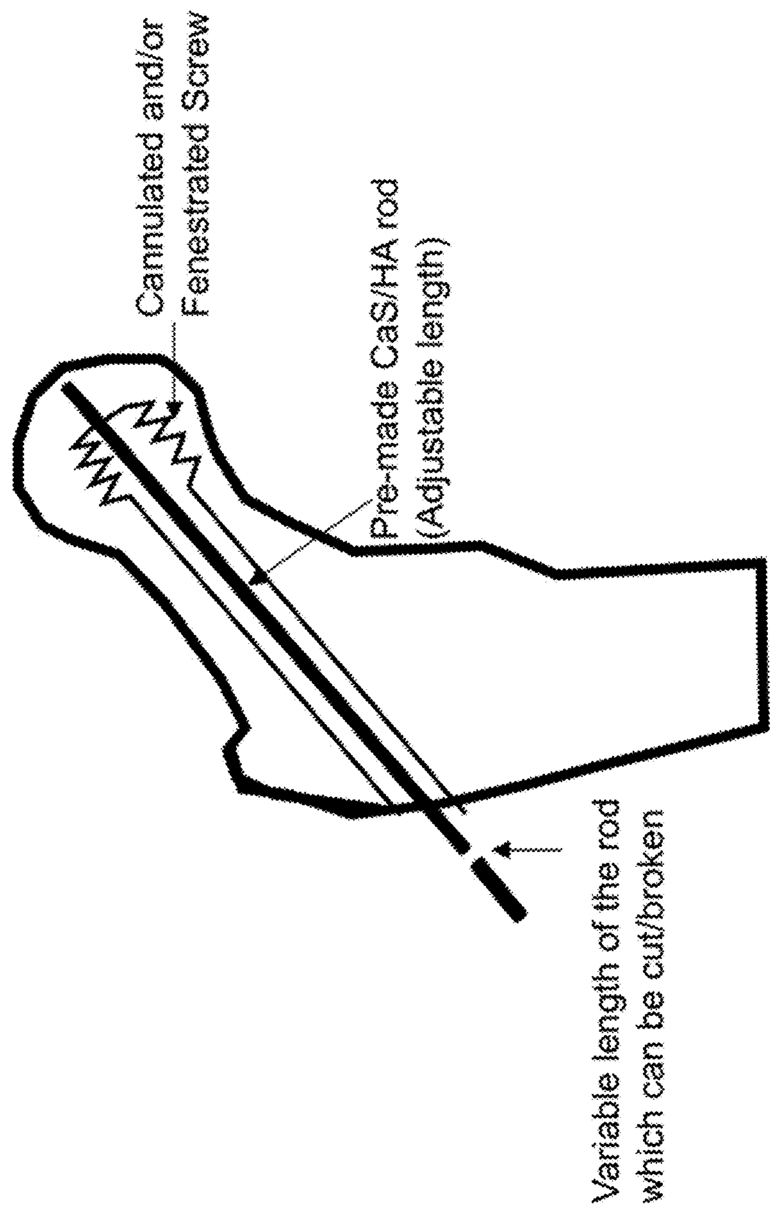

FIG. 27 illustrates a pre-made, set rod of CaS/HA that can be inserted in a cannulated or a cannulate/fenestrated screw to provide a recruiting apatite moiety for different apatite seeking drugs.

Figure 28:
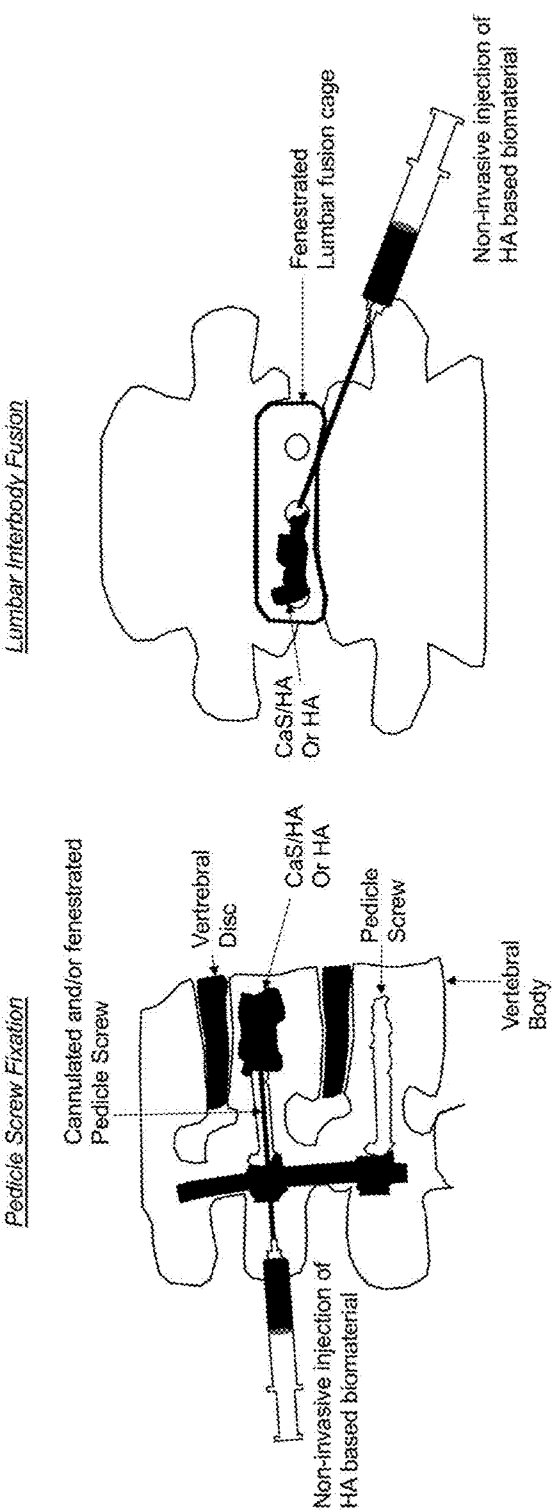

FIG. 28 illustrates a schematic of non-invasively delivering hydroxyapatite-based material into the bone for spinal applications.

Figure 29:
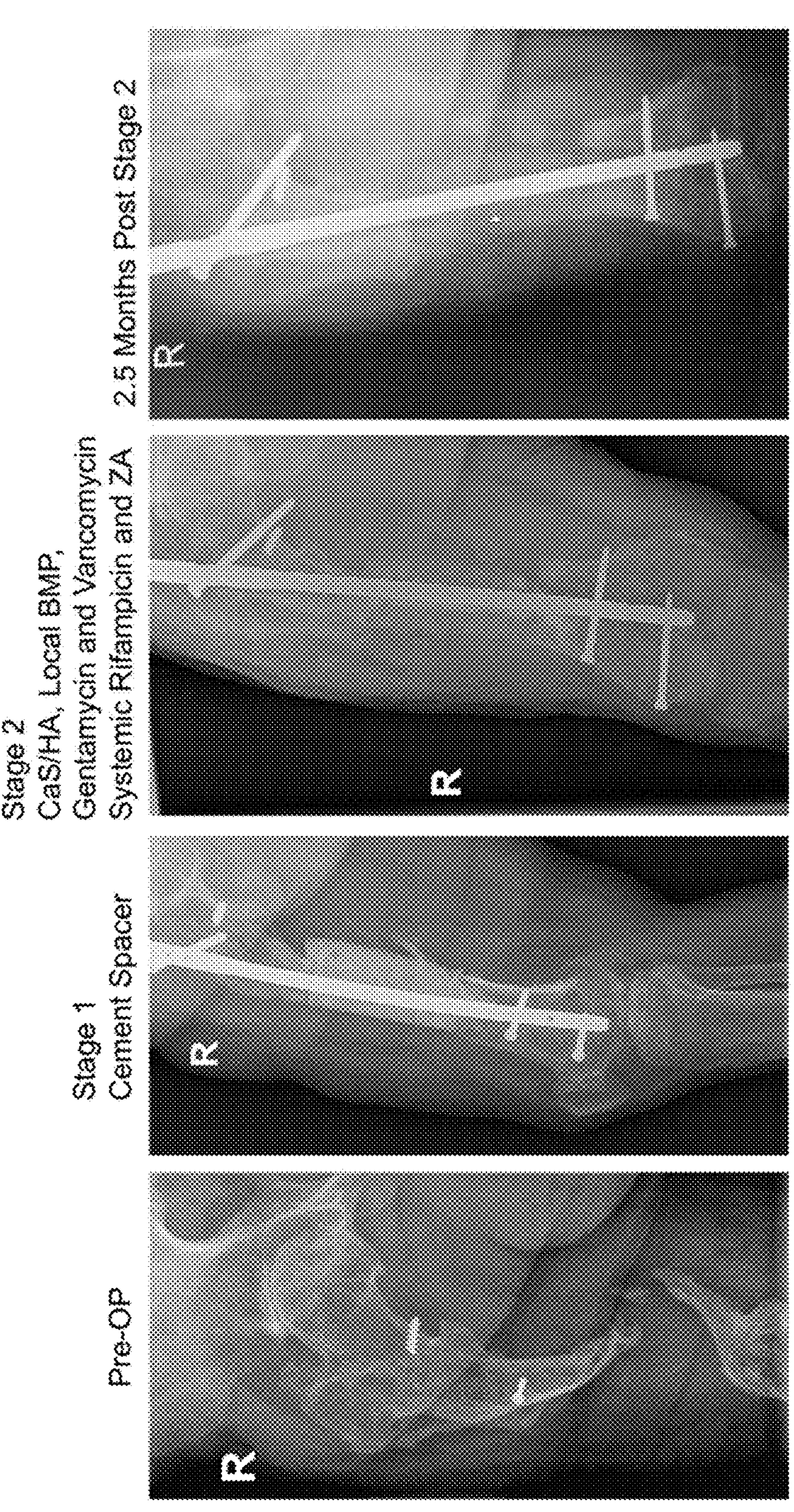

FIG. 29 illustrates a clinical case indicating the advantages of having an apatite based matrix that acts as seeking moiety for antibiotics and bone active agents.

DETAILED DESCRIPTION OF THE INVENTION

Present invention relates to the use of one or more materials. The material may be mono-phasic or comprising different phases, such as e.g. bi-phasic, tri-phasic, tetra-phasic, penta-phasic etc. In the context of the invention the material has to have at least one component that is not bioresorbable or very slowly bioresorbable.

By the term "bioresordable" or bioresorbable" is meant a material that can be broken down and absorbed by the body, and thus does not need to be removed manually. Such material may e.g. be integrated by the body, such as e.g. be integrated into bone tissue, or otherwise metabolized by the organism.

One non-limiting example is apatite or hydroxyapatite (HA) or any suitable bone substitute material (alloplasts). These materials are slowly bioresorbable any may eventually be integrated into the bone tissue of the subject. Other examples are autologous bone grafts (autograft) or cancellous bone. Moreover, various other bone grafts may be used such as e.g. isografts, allografts, xenografts etc. These materials may have a wholly or partially crystalline microstructure. Another feature is that these materials according to the invention are finely divided into small particles such as e.g. micro or even nanoparticles. As a consequence thereof, the effective surface of a certain amount of such material is very large. It is to be noted that according to the invention the above described material may be denoted as a first material. The first material may comprise several different components such that e.g. HA (hydroxyapatite) is mixed with e.g. cancellous bone or any other suitable bone substitute material.

As mentioned above this material is absorbed very slowly by the organism. Typically, the period of absorption may be in the range of weeks, months and even years, such as e.g. about 2 weeks, such as e.g. about 3 weeks, such as e.g. about 4 weeks, such as e.g. about 5 weeks, such as e.g. about 6 weeks, such as e.g. about 7 weeks, such as e.g. about 2 months, such as e.g. about 3 months, such as e.g. about 4 months, such as e.g. about 6 months, such as e.g. about 8 months, such as e.g. about 10 months, such as e.g. about 12 months, such as e.g. about 18 months, such as e.g. about 2 years, or such as e.g. several years etc. after administration to the subject.

In one aspect, the first material is absorbed very slowly by the organism, such as e.g. about 6 months, such as e.g. about 8 months, such as e.g. about 10 months, such as e.g. about 12 months, such as e.g. about 18 months, such as e.g. about 2 years, or between about 6 months to about 2 years after administration to the subject. In a further aspect the first material is absorbed very slowly by the organism, such as e.g. about 6 months to about 2 years.

The first material may optionally be mixed with a second material. The second material may comprise one component or may be mixtures of several components. The relation between the first material and the second material is such that the second material is absorbed by the body of the subject at a higher rate than the first material. Non-limiting examples of a second material is one or more of fibrogen, dextran, hyaluronic acid, alfatachycalciferol, calcium sulphate (hemi-hydrate and/or di-hydrate), collagen, various forms of cellulose such as carboxymethyl cellulose (CMC) or sodium-CMC etc or other polysaccharides such as e.g. agarose. Such materials are usually absorbed by the body within a few days, week or months, such as e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g. about 6 weeks, such as e.g. about 7 weeks, such as e.g. about 2 months, such as e.g. about 3 months, or such as e.g. about 4 months etc.

In one aspect, the second material is usually absorbed by the body of the subject within e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g. about 6 weeks after administration to the subject.

In a further aspect, the second material is usually absorbed by the body of the subject within e.g. about 1 day to about 6 weeks after administration to the subject. In one aspect, the second material is usually absorbed by the body of the subject within about 6 weeks after administration to the subject.

In yet a further aspect, when the composition comprises a first and a second material, the first material is absorbed very slowly by the organism, such as e.g. in the range of weeks, months and even years, such as e.g. about 2 weeks, such as e.g. about 3 weeks, such as e.g. about 4 weeks, such as e.g. about 5 weeks, such as e.g. about 6 weeks, such as e.g. about 7 weeks, such as e.g. about 2 months, such as e.g. about 3 months, such as e.g. about 4 months, such as e.g. about 6 months, such as e.g. about 8 months, such as e.g. about 10 months, such as e.g. about 12 months, such as e.g. about 18 months, such as e.g. about 2 years, or such as e.g. several years etc., and wherein the second material is usually absorbed by the body within a few days, week or months, such as e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g. about 6 weeks, such as e.g. about 7 weeks, such as e.g. about 2 months, such as e.g. about 3 months, or such as e.g. about 4 months etc.

In a further aspect, when the composition comprises a first and second material, the first material is absorbed very slowly by the organism, such as e.g. about 6 months, such as e.g. about 8 months, such as e.g. about 10 months, such as e.g. about 12 months, such as e.g. about 18 months, such as e.g. about 2 years, or between about 6 months to about 2 years after administration to the subject, and wherein the second material is usually absorbed by the body of the subject within e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g. about 6 weeks, or within e.g. about 1 day to about 6 weeks after administration to the subject.

The material, being either a mono-phasic material or mixtures of several phases, may be formulated in any form, such as e.g. a liquid such as e.g. a suspension or solution, paste form, semi-solid, or a solid formulation. The first material may be dispersed in the second material, such as e.g. HA (hydroxyapatite) being dispersed or mixed in a paste of calcium sulphate (CaS). Solid formulations may be in any for such as e.g. tablets, pellets, beads, sticks etc. of any suitable size such as allowing implantation into the body of the subject or injection into the body of the subject. With respect to liquid or semi-solid compositions, these may be administered to the subject by means of injection or any other suitable means. The composition comprising the first and optionally a second material may be such that once administered to the subject, the composition cures into a solid at the site of administration. The administration of the composition may suitably be at the site of the body in need of treatment such as e.g. at or near fractured or diseased bone or near a tumour.

The material or composition according to the invention may optionally further comprises any suitable pharmaceutical compound, such that the material or composition according to the invention which is administered to the subject comprises a first material, and optionally a second material, and a pharmaceutically active compound.

It is also to be noted that the material or composition according to the invention may also be applied or adhered at least partly to any surface. The surface may be the surface of any object that is to be implanted into the body of the subject, such as e.g. hip or joint replacement etc., or may be deposited into e.g. the surface of a membrane, disc or pin to be implanted into the body of the subject. Other examples may be other devices or objects such as e.g. catheters, spinal cage, any grid or net-like construction, tubes of any kind, stents etc. that are implanted or inserted into the body for a limited or unlimited period of time. With respect to devices, any kind of prosthetics and implants may be envisaged. In one non-limiting example, such device may be e.g. an object in any form of metal, alloy, polymer, elastomers etc. suitable for implanting into the body of a subject in need. Suitably, the device may at least partly be coated with a composition according to the invention, i.e. a first particulate material optionally mixed with a further material or materials. In another aspect, the device to be implanted or inserted into the body of the subject in need is not coated with any particulate material. The device or implant may or may not be hollow, i.e. may or may not contain a lumen and may comprise at least one inlet and optionally one outlet. In one aspect, the device may be designed as a hollow screw. Optionally, the hollow implant may be further fenestrated. Such hollow implant may be implanted or inserted into the body of the subject and the composition according to the invention comprising a first and optionally a second material may be injected or administered in any suitable manner into the device or adjacent to the device. The composition according to the invention may be in form of a pellet, pin, rod or the likes and be inserted into or near the device in question. Alternatively, the composition may be injected as a paste or liquid into or near the implant or device which may optionally cure inside the implant or device.

In a further aspect, the implant, which may optionally be a screw, may be coated with a composition according to the invention, such as e.g. be coated with particles of the first material. In a further aspect, the device may be coated with particles of the first material and thereafter implanted into the subject in need. Thereafter, the composition according to the invention may be injected in and/or near the implant. Subsequently, a pharmaceutical composition may be administered to the subject.

In one aspect, the device or implant which may optionally be a screw, is inserted into the body of the subject in a pre-drilled hole or cavity of the tissue in question. Such tissue may in principle be any tissue such as e.g. soft tissue (such as e.g. muscle) or may be e.g. bone tissue. In one embodiment, the device is partially inserted into the pre-drilled hole such that there is a remaining cavity of the pre-drilled hole. Thereafter, the composition according to the invention is inserted into the device, and/or near the device. Thereafter, the device, which may be e.g a screw, is fully inserted into the pre-drilled hole. Consequently, present invention also relates to a method, wherein the method comprises the following steps:

a) pre-drilling a hole or creating a cavity in any body tissue,
b) partially inserting a device into said cavity or hole,
c) optionally administering a composition according to the invention comprising a first and optionally a second material,
d) fully inserting the device into said hole or cavity,
e) optionally administering a pharmaceutical composition to the subject.

The device may be coated with a first and optionally second material according to the invention. Optionally, the material coated onto the device may be pre-loaded with a pharmaceutical compound having an affinity to either of the first and/or second material. The first material may be e.g. HA and the second material may be e.g. calciumsulphate (CaS). As mentioned above, the device may have at least one inlet and thus may have at least one outlet which may be in the axial direction of the screw. In one aspect, the device is a screw of any suitable material which is constructed to have one inlet and one outlet. Optionally, the screw may be fenestrated and thus have at least one or more other penetrating holes in the radial orientation of the screw.

As mentioned herein, the composition according to the invention may be administered into any site of the body of the subject. Specific tissue may be any soft tissue or may be in bone tissue. As the composition may be administered to any part of the body, present invention also relates to and enables an in situ generated medical device. This may be achieved by administering systemically and/or locally of one or more pharmaceutical compositions to a targeted device thereby changing the device and to locally actively combat for instance tumours and/or infections.

In one aspect, the pharmaceutical composition being administered to the subject may be a pharmaceutical compound displaying high affinity to the first material. Such pharmaceutical composition may be further conjugated or derivatised with a further pharmaceutical compound that may have no or very low affinity for the first material. Such further pharmaceutical composition may be covalently or indirectly bound or complexed to the a pharmaceutical compound displaying high affinity to the first material. In one instance, the first material may be HA (hydroxyapatite). A suitable pharmaceutical compound having high affinity for HA may be, but not limited to, bisphosphonates. In this non-limiting case, the bisphosphonate may be further conjugated to or derivatised with e.g. an antibiotic, anti-cancer drug, fluorescent compound or a radioemitter. The radioemitter may be one or more same or different compounds and may be e.g. an alpha- or beta-particle radiating compound or a combination of the two. In such instances, the method may be used for local treatment of cancer in any tissue, bacterial infection or e.g. enabling visualization of an implant in the body of a subject.

Once the material or composition according to the invention has been administered to the subject, the second material (in case it is present) is absorbed by the body or erodes in the body of the subject so as to expose the finely particulate structure or the first material having a very high effective surface area. The period during which the absorption or erosion of the second material takes place varies with the material used as second material. Thus the period in questions may be at least a few hours, or within e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g. about 6 weeks, or within e.g. about 1 day to about 6 weeks after administration to the subject. After the absorption period of the second material, one or more pharmaceutical compositions may be administered to the subject. Consequently, one or more pharmaceutical compositions may be administered after at least a few hours, or within e.g. about 1 day, such as e.g. about 2 days, such as e.g. about 3 days, such as e.g. about 4 days, such as e.g. about 5 days, such as e.g. about 6 days, such as e.g. about 7 days, such as e.g. about 8 days, such as e.g. about 9 days, such as e.g. about 10 days, such as e.g. about 11 days, such as e.g. about 12 days, such as e.g. about 13 days, such as e.g. about 2 weeks, such as e.g. about 3 weeks, such as e.g. about 4 weeks, such as e.g. about 5 weeks, such as e.g.

about 6 weeks, or within e.g. about 1 day to about 6 weeks after the first and/or second material has been administered to the subject.

Alternatively, the one or more pharmaceutical compositions are administered e.g. about 2 weeks, such as e.g. about 3 weeks, such as e.g. about 4 weeks, such as e.g. about 5 weeks, such as e.g. about 6 weeks after administration of the composition according to the invention.

Alternatively, the one or more pharmaceutical compositions are administered e.g. about 6 weeks to about 1 year, about 18 months, or about 2 years after administration of the composition according to the invention.

The one or more pharmaceutical compositions may be administered one or more times, such as e.g. 2 or more time, 3 or more times, 4 or more times, 5 or more times, 6 or more times, 7 or more times, 8 or more times, 9 or more times, 10 or more times etc.

The one or more pharmaceutical compositions may comprise two or more different active ingredients, such as 3 or more, 4 or more, or 5 or more etc. Such active ingredients may display different affinities toward the first and the second material.

In the regimen relating to administration of one or more pharmaceutical compositions, the pharmaceutical composition may comprise one or more same or different active ingredients at the first instance of administration, whereas upon a second administration, the pharmaceutical composition may comprise one or more same or different active ingredients, which are optionally different from the ones administered at the first instance or occasion of administration of a pharmaceutical composition.

In such instance no second material is employed, such as e.g. when the first material is deposited on a surface without a second material.

After the period which the absorption or erosion of the second material has taken place, a suitable pharmaceutical compound is administered. It is to be noted that there are numerous examples in prior art on routine administration of e.g. antibiotics administered post- and/or pre-operatively. However, the aim with such procedure in prior art is merely to prevent infection that may arise upon insertion of e.g. an implant into the body of a subject. On the contrary, the inventors of present invention have surprisingly discovered that systemic administration of certain pharmaceutical compounds/composition will seek out the composition according to present invention, i.e. the first and optionally second material, once the activated surface of the first material is being exposed by erosion of the second material.

As mentioned above, the inventors of present invention have surprisingly found that by administering the material or composition to a subject and thereafter allowing a certain period to pass, it is possible to thereafter administer a pharmaceutical compound to the subject. Furthermore, the inventors have found that the pharmaceutical compound may be administered in the conventional way being standard for the pharmaceutical compound or composition in question, such as e.g. oral or intravenous administration. Thus the pharmaceutical compound will enter the systemic circulation of the subject but will be concentrated and attracted to the first material with an exposed high surface area. Consequently, the innovative method may be seen as a site directed treatment where the one or more pharmaceutically active compounds seek up and directly or indirectly bind to or concentrates at the site or surface of the first material. Consequently, present invention provides for a more effective treatment allowing the for new treatment regimens based on known active pharmaceutical compounds to be administered in the conventional way already approved by the authorities and consequently omits some of the requirements of clinical testing and evaluation of a composition which has not been approved by the authorities, i.e. where the pharmaceutical compound is formulated in a novel way and also possibly to be administered in a manner not previously tested.

A further consequence of present invention is that the innovative method disclosed herein provides for a higher concentration of the pharmaceutical composition at the site in question, i.e. the concentration of the pharmaceutical composition becomes higher at the site due the chemotactic affinity to the first material and a highly activated surface. This provides for a more efficient treatment regimen with many benefits. On the other hand, since in one aspect of the invention, the material or composition according to the invention attracts the administered pharmaceutical compound, the local concentration is in many instances optimized and decreasing or eliminating complications. One such example is prosthetic joint infections, wherein it has been shown that the very high local concentrations achieved with local antibiotic ceramic carriers can prevent and eradicate bio-film bacteria which is a major issue in prosthetic joint infections.

The one or more pharmaceutical compounds according to the invention may in principle be any pharmaceutical compound that shows an affinity for the first material used in the composition according to the invention. In one aspect, the pharmaceutical compound may be any pharmaceutical compound showing an affinity for hydroxyapatite particles.

As mentioned above, the treatment may comprise the use of one or more same or different classes of pharmaceutical compounds. These may either be administered concurrently or sequentially in any order as needed or deemed necessary.

Present invention also relates to a composition, wherein the one or more administered drugs display different affinities towards the first and the second material. Thus in one aspect, present invention relates to a bi-phasic or multiphasic composition, various different pharmaceutical compounds may be employed such that e.g. one pharmaceutical compound shows high affinity towards the particulate first material (and low affinity towards the second material), and another pharmaceutical compound shows high affinity towards the second material (and low affinity towards the first material) etc. In one aspect, the second material may be mixed or pre-loaded with a pharmaceutical compound which optionally shows high affinity for the second material, and then further mixed with the first material. Also, alternatively, the first material may be mixed or exposed to a pharmaceutical compound displaying high affinity to the first material. The above mentioned first and second materials may be mixed and administered to the subject in need. This allows for a method or treatment regimen where one pharmaceutical compound very slowly is allowed to be released from the composition according to the invention (the first material), whereas one pharmaceutical compound is released relatively quickly from the second material which is eroded relatively quickly be the body of the subject in question. In one non-limiting example, the first material may be hydroxyapatite and the second material may be calcium sulphate.

In one aspect, present invention also relates to a composition comprising a first particulate material, wherein the material in in nano-sized particles. The material may or may not be pre-loaded with a pharmaceutical compound. Such particles may be administered as a suspension or otherwise dispersed in any suitable solvent such as e.g. as saline solution, which is suitably a physiological saline solution. Such composition may be used for various applications such as e.g. administration into or near a tumour or infected tissue, where the particles will penetrate the bacterial or cancerous cells to exert their action.

The pharmaceutical compound may be any antibiotic compound such as e.g. rifampicin or any ansamycin such as e.g. geldanamycin, herbimycin A, macbecin, natalamycin, streptovaricin or rifamycins in general or any derivatives thereof. The antibiotic compound may also be a daptomycin.

The antibiotic may be any type of fluoroquinolone, such as e.g. flumequine, oxolinic acid, rosoxacin, ciprofloxacin, fleroxacin, lomefloxacin, nadifloxacin, norfloxacin, ofloxacin, pefloxacin, rufloxacin, balofloxacin, levofloxacin, trovafloxacin, grepafloxacin, levofloxacin, pazufloxacin, sparfloxacin, temafloxacin, clinafloxacin, gatifloxacin, moxifloxacin, sitafloxacin, prulifloxacin, besifloxacin, delafloxacin, ozenoxacin, danofloxacin, difloxacin, enrofloxacin, ibafloxacin, marbofloxacin, orbifloxacin, and sarafloxacin or nalidixic acid, or any combinations thereof.

In one aspect the antibiotic may be any type of β-lactam, such as e.g. penicillin, benzathine penicillin, benzylpenicillin, phenoxymethylpenicillin, procaine penicillin, cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin, piperacillin, cefazolin, cephalexin, cephalosporin C, cephalothin, cefaclor, cefamandole, cefuroxime, cefotetan, cefoxitin, cefixime, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, aztreonam, tigemonam, nocardicin A, tabtoxinine β-lactam, clavulanic acid, tazobactam, sulbactam, avibactam,or any combinations thereof.

In one aspect the antibiotic may be any type of glycopeptide such as e.g. vancomycin, teicoplanin, or ramoplanin, or any combinations thereof.

In a further aspect, the antibiotic may be a lipopeptide such as e.g. bacillomycins, daptomycin, echinocandins (e.g., caspofungin), iturin A, mycosubtilin, surfactin, or any combinations thereof.

In yet a further aspect the antibiotic may be an aminoglycoside such as e.g. amikacin, apramycin, arbekacin, astromicin, bekanamycin, dibekacin, dihydrostreptomycin, elsamitrucin, fosfomycin/tobramycin, gentamicin, hygromycin B, isepamicin, kanamycin A, kasugamycin, legonmycin, lividomycin, micronomicin, neamine, neomycin, netilmicin, nourseothricin, paromomycin, plazomicin, ribostamycin, sisomicin, streptoduocin, streptomycin, tobramycin, totomycin, and verdamicin, or any combinations thereof.

In one aspect, the antibiotic may be a teratcyclin of any kind, such as e.g. tetracycline, chlortetracycline, oxytetracycline, demeclocycline, lymecycline, meclocycline, methacycline, minocycline, rolitetracycline, tigecycline, omadacycline, sarecyclin or any combinations thereof.

In one aspect, the antibiotic may be a macrolide, such as e.g. azithromycin, clarithromycin, erythromycin, fidaxomicin, telithromycin or any combinations thereof.

In one aspect, the antibiotic may be a any type of oxazolidinone such as e.g. eperezolid, linezolid, posizolid, radezolid, ranbezolid, sutezolid, tedizolid or any combinations thereof.

The pharmaceutical compound may also be a bisphosphonate such as e.g. zoledronic acid, etidronic acid, clodronic acid, tiludronic acid, pamidronic acid, neridronic acid, olpadronic acid, alendronic acid, ibandronic acid, risendronic acid or any suitable slats thereof. The bisphosphonate be also be a salt wherein a radioactive compound is present or a radioactive compound as $^{99}$Tc or $^{223}$Ra or strontium or samarium.

Other agents may be employed are e.g. compounds that are X-ray visible or detectably by standard means such as e.g. fluorescence or MR or compounds used in PET-CT. One example is e.g. compounds comprising $^{18}$F such as e.g. Na$^{18}$F or fluorodeoxyglucose ($^{18}$F).

Thus according to the methods of present invention, areas of clinical interest may in particular be bone regeneration, treatment of bacterial infections of any kind, and e.g. anticancer treatment.

It is to be understood that the administration of the material or compound according to the invention may into any tissue such as any soft tissue or organ or may be administered near or into bone tissue.

With respect to administration of the pharmaceutically active compound, it is to be understood that any conventional method of administration may be employed which has been previously approved by clinical authorities. If for example a drug has been approved for oral administration, the same administration rout may be employed according to the invention. Thus, the administration is usually results in the pharmaceutically active compound entering the systemic circulation of the subject. As previously mentioned, the administration may be e.g. oral or intravenous.

In another aspect of the invention, the pharmaceutically active compound may be administered near or into e.g. an implant. In such instance, the pharmaceutically active compound may be deposited in any form of formulation and be e.g. injected near the implant or deposited into the surface of a pin, or absorbed in any suitable carrier that is inserted into cavities of the implant. The pin, may be broken off after insertion into the implant.

As mentioned herein the first material used according to the invention has to be in a finely divided solid state, such as e.g. in small particles so as to provide for a high effective surface. The first material may be such that 1 ml of the material contains at least 0.5 million particles, such as e.g. at least 1 million particles, such as e.g. at least 2 million particles, such as e.g. at least 3 million particles, such as e.g. at least 4 million particles, such as e.g. at least 5 million particles, or such as e.g. at least 10 million particles. In one aspect, the first material according to the invention is apatite or hydroxyl apatite.

The particles according to the invention may be in range of microparticles or nanoparticles. The size of these particles may be e.g. The particle size is preferably e.g. less than 200 μm, such as less than 100 μm, less than 50 μm, less than 35 μm, less than 20 μm or less than 10 μm. Moreover, the particles may be between about 0.1 and about 50 μm. In another aspect the microparticles may be in range of about 1 μm to about 500 μm, such as e.g. about 1 μm to about 100 μm, about 1 μm to about 50 μm, about 1 μm to about 25 μm, about 1 μm to about 15 μm, about 1 μm to about 10 μm, or about 1 μm, about 5 μm, about 10 μm, about 15 μm, about 20 μm, about 25 μm, about 30 μm, about 35 μm, about 40 μm, about 45 μm, about 50 μm, about 75 μm, about 100 μm, about 500 μm etc.

In one aspect, the particles of the first material is in range of e.g. about 1 μm to about 10 μm.

It has been surprisingly found that micro sized particles display a higher affinity for an administered drug than particles of larger or smaller size than micro sized particles of the first material. The drug may suitably be administered systemically.

In a preferred embodiment, the drug may be administered once and once only and the the particles in the first material are micro sized particles.

As mentioned herein, the administered drug or drugs may be administered several times at different occasions as deemed necessary by the clinicians.

In yet a further aspect, the particle size may be in range of e.g. about 1 nm to about 200 nanometres (nm), such as e.g. less than about 150 nm, less than about 100 nm, less than about 50 nm, less than about 45 nm, less than about 40 nm, less than 35 nm, less than about 30 nm, less than about 25 nm, less than about 20 nm, less than about 15 nm, or less than about 10 nm. In one aspect the particle size is in range of e.g. about 1 nm to about 100 nm. In a further aspect, the particles of the first material may be about 1 nm, such as e.g. 5 nm, such as e.g. about 10 nm, such as e.g. about 15 nm, such as e.g. about 20 nm, such as e.g. about 25 nm, such as e.g. about 30 nm, such as e.g. about 35 nm, such as e.g. about 40 nm, such as e.g. about 45 nm, such as e.g. about 50 nm, such as e.g. about 100 nm, such as e.g. about 150 nm, or such as e.g. about 200 nm.

In one aspect, the particle size may be in range of about 40 nm to about 100 nm.

It has been surprisingly discovered by the inventors of present invention that in such instances that multiple administration of a drug or drugs is deemed necessary, the affinity towards nano-sized particles in the first material is higher for nano-sized particles in the sense that upon additional administration (i.e. repeated administration) of one or more pharmaceutical compositions, nano-sized particles of the first material displays a higher affinity than larger micro-sized particles. It thus appears that repeated administration of one or more pharmaceutical compounds re-loads the nano-sized particles in the first material.

In another aspect, the first material according to the invention may be a composition comprising a mixture or micro-sized particles and nano-sized particles. Thus the first material may comprise at least partly particles in the range of about 1 μm to about 500 μm, such as e.g. about 1 μm to about 100 μm, about 1 μm to about 50 μm, about 1 μm to about 25 μm, about 1 μm to about 15 μm, about 1 μm to about 10 μm, or about 1 μm, about 5 μm, about 10 μm, about 15 μm, about 20 μm, about 25 μm, about 30 μm, about 35 μm, about 40 μm, about 45 μm, about 50 μm, about 75 μm, about 100 μm, about 500 μm etc, and/or particles in the range of e.g. 1 and 200 nanometres (nm), such as e.g. less than 100 nm, less than 50 nm, less than 35 nm, less than 20 nm or less than 10 nm. In one aspect the particle size is in range of e.g. about 100 nm to about 1 nm.

Thus, in one aspect, the composition according to the invention may comprise only a first material as disclosed herein. As mentioned herein the first material may be e.g. HA. The first material may be a mixture of micro-sized particles and nano-sized particles as mentioned herein, and consequently may be a mixture of micro-sized particles or nano-sized particles, or a combination of micro-sized particles and nano-sized particles. For example, micro-sized particles may be in range of about 1 μm to about 500 μm, or about 1 μm to about 10 μm, and wherein the nano-sized particles may be in range of about 1 nm to about 200 nm, or about 40 nm to about 100 nm.

In another aspect, present invention relates to a composition comprising first and a second material as disclosed herein. The first material may be a mixture of micro-sized particles and nano-sized particles as mentioned herein. In one example, the first material may be a mixture of micro-sized particles and nano-sized particles as mentioned herein, and consequently may be a mixture of micro-sized particles or nano-sized particles, or a combination of micro-sized particles and nano-sized particles. For example, micro-sized particles may be in range of about 1 μm to about 500 μm, or about 1 μm to about 10 μm, and wherein the nano-sized particles may be in range of about 1 nm to about 200 nm, or about 40 nm to about 100 nm.

Various ratios and relations between the amount of micro-sized and nano-sized particles may be present in a composition according to the invention. For example, the relation between the various partciles sizes may be in range of about 1% (wt %) to about 99.9% (wt %) between nano: micro-sized particles, such as e.g. about 10% to about 90%, about 15% to about 85%, about 20% to about 80%, about 25% to about 75%, about 30% to about 70%, about 35% to about 65%, about 40% to about 60%, about 45% to about 55%, or about 50% to about 50%, about 55% to about 45%, about 60% to about 40%, about 65% to about 35%, about 70% to about 30%, about 75% to about 25%, about 80% to about 20%, about 85% to about 15%, about 90% to about 10%, about 95% to about 5%, or about 99.9% to about 1%. In one aspect, the ratio or relationship is about 50% to about 50% between nano: micro-sized particles. In one further aspect, the invention relates to a composition according to the invention wherein about 33.3% are micro-sized particles, 33.3% are nano-sized particles, and the remaining about 33.3% may be midsized particles which are not overlapping with the particle size intervals of the micro-sized and nano-sized particles.

In another aspect, the inventors of present invention have found that a certain amount of the first material is capable of binding a certain amount of the administered drug or drugs. In one non-limiting example, the first material may be hydroxyapatite. The amount of the first material may be e.g. at least about 1 mg, such as e.g. at least about 5 mg, such as e.g. at least about 10 mg, such as e.g. at least about 15 mg, such as e.g. at least about 20 mg, such as e.g. at least about 25 mg, such as e.g. at least about 30 mg, such as e.g. at least about 35 mg, such as e.g. at least about 40 mg, such as e.g. at least about 45 mg, such as e.g. at least about 50 mg. Alternatively, the amount of the first material may be in range of about 1 mg to about 50 mg, such as e.g. 5 mg to about 40 mg, such as e.g. about 5 mg to about 35 mg, such as e.g. about 5 mg to about 30 mg, such as e.g. about 5 mg to about 25 mg, such as e.g. about 5 mg to about 20 mg, such as e.g. about 5 mg to about 15 mg, such as e.g. about 5 mg to about 10 mg. As a further alternative, the amount of the first material in a composition according to present invention may be about 5 mg, such as e.g. about 10 mg, such as e.g. about 15 mg, such as e.g. about 20 mg, such as e.g. about 25 mg, such as e.g. about 30 mg, such as e.g. about 35 mg, such as e.g. about 40 mg, such as e.g. about 45 mg, such as e.g. about 50 mg.

It has been found that micro-sized as well as nano-sized particles of the first material, which in one aspect may be hydroxyapatite, in the amount of about 5 mg is capable of binding about 10% of the administered drug. It has further been found that 10 mg of the first material is capable of binding about 30% of the administered drug and that 20 mg of the first material is capable of binding about 75% of the administered drug. In another aspect, it has been found that about 30 mg to about 40 mg is capable of binding nearly 100% of the administered drug. Thus, in one aspect the amount of the first material is preferably in range of about 30 mg to about 40 mg. The amount of the first material is to be understood as the amount being optionally mixed with the second or even third material, that may be in other ranges of amounts, in a composition according to the invention.

The ratio between the first and the second material may be in range of about about 1% to about 99.9% between first material: second material, such as e.g. about 10% to about 90%, about 15% to about 85%, about 20% to about 80%, about 25% to about 75%, about 30% to about 70%, about 35% to about 65%, about 40% to about 60%, about 45% to about 55%, or about 50% to about 50%, about 55% to about 45%, about 60% to about 40%, about 65% to about 35%, about 70% to about 30%, about 75% to about 25%, about 80% to about 20%, about 85% to about 15%, about 90% to about 10%, about 95% to about 5%, or about 99.9% to about 1%. In one aspect, the composition comprises only a first material. In one aspect, the ratio or relationship is about 40% to about 60% between first material: second material. In one non-limiting example, the first material may be e.g. HA (hydroxyapatite) in an amount of 40% (wt %) and the second material may be e.g. CaS (calcium sulphate) in an amount of 60% (wt %).

In one aspect, the first material such as e.g. calcium phosphate is provided as calcium phosphate particles (e.g. sintered hydroxyapatite particles) to be mixed with the second material such as e.g. calcium sulphate powder and water for the calcium sulphate to set, whereby the calcium phosphate particles becomes embedding in the calcium sulphate phase after setting. The water may be seen as a non-limiting example of a third material. A third material may be any additional solvent or further solid substance acting as diluent or mixing agent to the first and optionally the second material.

The composition according to the invention may comprise a first and optionally a second material. The first material may be administered as a particulate material which may optionally be in form of an emulsion, dispersion, solution etc. In such case, optionally a further diluent is added which acts as a carrier to the first material.

In another aspect, the composition according to the invention comprises a first and a second material. The composition may then be prepared by conventional mixing known in the art, which may further comprise addition of a solvent or other diluent. In one example, the mixing of the components of the composition may take place at normal room temperature and/or under normal atmospheric pressure. Alternatively, the mixing may take place under vacuum or reduced atmospheric pressure. It has been observed that the wettability affecting chemical binding of the finished composition is increased by mixing under vacuum or reduced atmospheric pressure.

In one aspect, the first and/or second and/or third material may further comprise other active ingredients such as e.g. anabolic factors active in bone formation, i.e. preferably bone growth proteins selected from the group comprising bone morphogenic proteins (BMPs), insulin-like growth factors (IGFs), transforming growth factor-ps (TGFPs), parathyroid hormone (PTH), sclerostine, and the like. The bone active proteins may also be provided in the form of a composition comprising cell factory-derived bone active proteins, and ECM proteins (WO 2008/041909). Alternatively strontium as a bone growth factor may be used in addition to or as a substitute of the bone active proteins. In one aspect, the bone active protein could be bone growth proteins selected from the long list of BMPs, but most preferably BMP-2 or BMP-7 or a combination thereof. BMPs may be isolated from donor cells (e.g. from a bone cell factory) or prepared recombinantly. For human patients recombinant human BMPs, such as rhBMP-2 or rhBMP-7 are preferably used. rhBMPs are commercially available or may be produced by known techniques.

In one aspect of the invention, anti-catabolic agents useful in the composition of the present invention are agents which inhibit bone resorption. Non limiting examples of inhibitors with bone resorption properties are bisphosphonates, selective estrogen receptor modulators (SERM) (e.g. raloxifene, tamoxifen, lasofoxifene and bazedoxifene); denosumab (a monoclonal antibody against RANKL developed by Amgen) and statins.

In one aspect, the composition according to the invention may further comprise an X-ray contrast agent selected from water soluble non-ionic X-ray contrast agents (e.g. iohexol) and/or biodegradable X-ray contrast agents. The X-ray contrast agent may be mixed with the calcium sulphate powder, the calcium phosphate powder, other additives or with the liquid, or may be mixed with the paste comprising the calcium sulphate powder, the calcium phosphate powder and the liquid in a delayed mixing process as described above. X-ray contrast agents may also be encapsulated in water-soluble and/or biodegradable synthetic polymeric microcapsules, bovine collagen particles, starch particles, dihydrate nidation particles, or the like, if desirable. The X-ray agent(s) may be provided in the same or different encapsulations optionally with the anti-catabolic agent and/or the bone active protein and/or other additives and released before or in the paste. A premixed X-ray solution comprising iodine (iohexol) for enhancing x-ray capacity ready for mixing with ceramic powders is available from BONESUPPORT AB under the trade name CERAMENT™IC-TRU.

In one aspect, the invention relates to a method of loading one or more pharmaceutical compounds onto the first and/or second material of present invention. Such method may comprise the steps of:

a) providing a particulate first material and/or a second material,
b) contacting/incubating one or more pharmaceutical compounds with the material in a),
c) separating non-bound pharmaceutical compounds from the material obtained in step b).

The one or more pharmaceutical compounds may be same or different and may have different affinities for the first and second material. The one or more pharmaceutical compounds may be dissolved in any suitable solvent such as a physiological saline solution, water or other aqueous solution, buffered solution, or any suitable organic solvent or any mixtures thereof.

The period during which the one or more pharmaceutical compounds is contacted with the particulate first material and/or a second material, may be within range of minutes, hours or days, such as e.g. about 1 hour, such as e.g. about 3 hours, such as e.g. about 6 hours, such as e.g. about 12 hours, such as e.g. about 24 hours, such as e.g. about 48 hours etc.

After contacting/incubating the one or more pharmaceutical compounds with the particulate first material and/or a second material, the resulting mixture may be separated from the solution or suspension comprising the one or more pharmaceutical compounds by centrifugation or filtration etc. the resulting particulate material may be rinsed with any suitable solvent and optionally thereafter allowed to dry.

The invention is further illustrated in the following non-limiting examples.

EXAMPLES

General Experimental Procedure

CaS and HA powder is mixed at a ratio of 60 and 40% wt. Water or radiographic contrast agent is mixed at a liquid to powder ratio of 0.43 mL/g. The liquid and the powder components are mixed rigorously to produce a homogenous slurry. This slurry can be casted into any shape by injecting it into a mould. In about 6-12 mins, the material sets into a hard mass. Alternatively, the slurry may be injected or inserted into the body of the subject.

Example 1

In an In Vivo Study a Fenestrated PEEK Implant was Filled with a Ceramic Carrier (Calcium Sulphate (CaS)/Hydroxy-apatite (HA)) and Implanted in the Tibial Bone of Rats.

Figure 1:
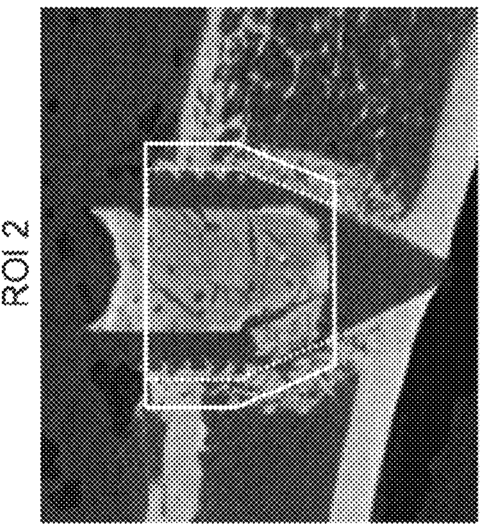
FIG. 1 illustrates regions of interest (ROIs) used for the quantification of bone formation around the implant.
Figure 1:
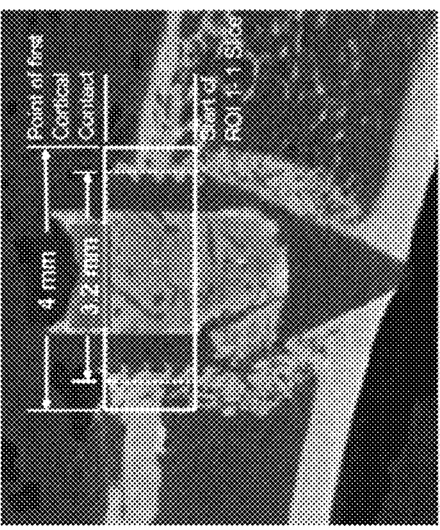
Figure 1:
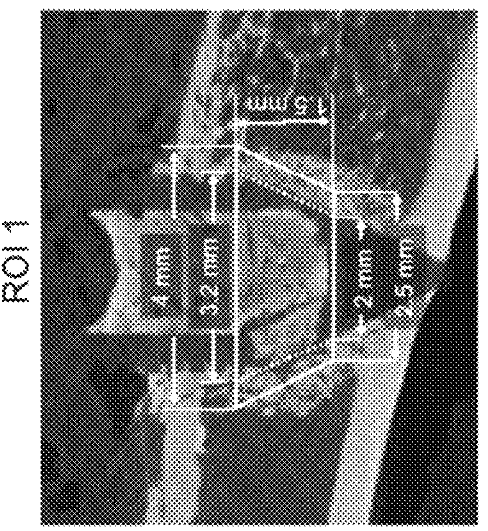

Methods: The PEEK implant was a hollow cylinder, with three holes at the bottom, to allow for filling with the CaS/HA biomaterial. Three experimental groups were used: 1) Implant alone (G1), 2) Implant containing CaS/HA in the hollow cavity followed systemic administration of ZA, 2-weeks post implantation (G2) and 3) Implant containing CaS/HA and ZA locally within the hollow cavity (G3). The systemic dose of ZA was 0.1 mg/kg and the local ZA dose was 10 μg. 6-weeks post surgery, the animals were sacrificed and the bone subjected to x-ray and micro computed tomography to quantify the extent of peri implant bone formation. Two regions of interest (ROIs) were used FIG. 1.

Figure 2:
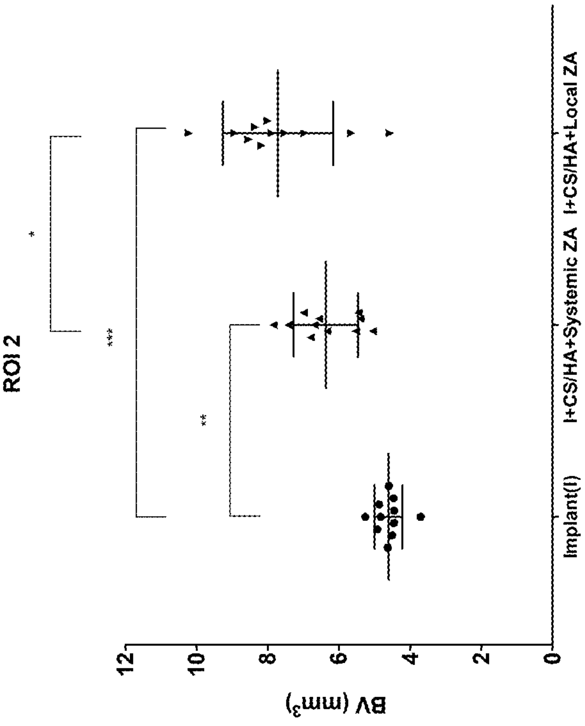
FIG. 2 illustrates micro-CT results from the implant study 6-weeks post implantation. Left graph shows results from the first region of interest (ROI), which was chosen to be immediately around the implant holes. The image on the right presents data from ROI 2, which quantified bone growth around the entire depth of the chamber. The amount of bone formation was significantly higher in groups G2 (systemic ZA) and G3 (local ZA) when compared to G1 (only implant) p-value<0.01 (FIG. 2). No differences in G2 and G3 were seen in ROI 1 but bone formation was higher in G3 compared to G2 in ROI 2.
Figure 2:
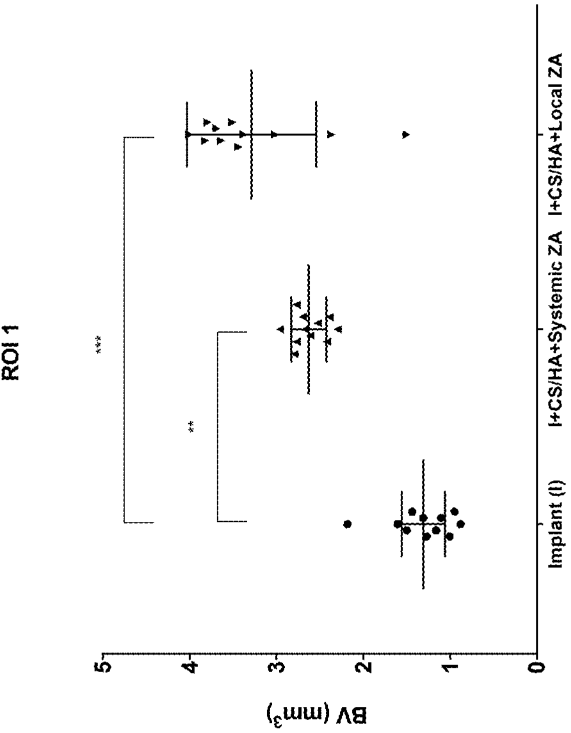

The implant integration with the surrounding bone was evaluated using pull-out testing on an Instron/MTS machine. Peak pull-out force, stiffness and absorbed energy was computed from this test. Results are illustrated in FIG. 2 Statistically significant peak force to pull-out the implant from the tibia was observed in groups G2 (systemic ZA) and G3 (local ZA) when compared to the only implant group G1 ($p<0.01$) (FIG. 3). No differences in the stiffness were seen. Absorbed energy was significantly higher in the local ZA group (G3) when compared to the only implant group (G1) ($p<0.05$). These findings were also confirmed using histology (FIG. 4). More bone formation was observed in groups G2 and G3 compared to G1.

This example illustrates that apatite in the CaS/HA biomaterial filled within the PEEK implant acts as a seeking moiety for the bioactive drug, zoledronic acid (ZA). Due to chemotaxis, to the carrier and leakage of ZA from the Peek holes there is an increased bone formation around the implant in group G2 (systemic ZA) when compared to the only implant group, G1.

Example 2

ZA Seeks the Apatite-Based Material in a Muscle.

Methods: A pellet of CaS/HA biomaterial (5 mm diameter×2 mm height) was placed in an abdominal muscle pouch of rats. 2-weeks after surgery, the animals were injected with $^{14}$C labelled ZA (0.1 mg/kg, specific radioactivity: 7.1 MBq/mL) via the systemic route (sub-cutaneous) and the radioactivity was measured in 1) the CaS/HA pellet placed in the muscle and 2) surrounding muscle 24-h later.

Results: The uptake of $^{14}$C-ZA was obvious in the CaS/HA biomaterial. The muscle surrounding the implant had very low radioactive counts as shown in FIG. 5.

This verifies that radioactive ZA seeks the apatite-based biomaterial outside bone and verifies the findings from the bone implant model in Example 2.

Example 3

Accretion and Long-Term Availability of the $^{14}$C-ZA in the CaS/HA Biomaterial.

Methods: The CaS/HA biomaterial was implanted in the femoral neck canal of 6 osteoporotic rats. The animals (n=3) then received a systemic (sub-cutaneous) dose of $^{14}$C-ZA (0.1 mg/kg, specific radioactivity: 7.1 MBq/mL) 2-weeks post implantation. The animals were sacrificed 6 months post implantation (5 months and 2 weeks post injection).

Results: The uptake of $^{14}$C-ZA in the animals that were given a systemic dose of $^{14}$C-ZA was verified using scintillation counting. Results are illustrated in FIG. 6.

This example confirms that $^{14}$C-ZA seeks and stays in the apatite material for at least 6-months post injection.

Example 4

Antibiotic Tetracycline with Known Fluorescence and Affinity to Bone Bind to Particulate Apatite in a Muscle.

Methods: A pellet of CaS/HA biomaterial (5 mm diameter×2 mm height) was placed in an abdominal muscle pouch of rats. 2-weeks after surgery, the animals were injected with tetracycline via the systemic route (sub-cutaneous) (Concentration 25 mg/kg, 8 mg injected/rat). 1-day later, the animals were sacrificed and the pellet of CaS/HA as well as surrounding muscle was harvested, fixed in formalin (4%) and embedded in paraffin. The tissue was then cut using a microtome to a thickness of 5 μm. The sections were deparaffinized using xylene, rehydrated using decreasing ethanol gradient and cleared in water. Finally, the sections were analyzed on a fluorescence microscope (Zeiss, Japan Filter: FITC, Gain: 0, Exposure: 150 ms).

The results indicate a clear uptake of the antibiotic in the CaS/HA biomaterial but no uptake was seen in the surrounding muscle indicating a clear affinity of tetracycline to particulate HA in the biomaterial (results are illustrated in FIG. 7).

Example 5

18-F, a Radioactive Bone Seeking Isotope, Accumulates and Can Be Traced in the Apatite Moiety in a Non-Orthotopic Site-Muscle.

Methods: A pellet of CaS/HA biomaterial (5 mm diameter×2 mm height) was placed in an abdominal muscle pouch of rats. 2-weeks after surgery, the animals were injected with $^{18}$F-Fluoride via the tail vein (Specific radioactivity: 120 MBq). The uptake of the tracer in the apatite-based material was evaluated 1 h 45 min later using positron emission tomography (PET) combined with micro-computed tomography (micro-CT). The total scan time was 20 min.

Results: From the PET-CT experiment, it verifies accretion of the systemically given $^{18}$F-Fluoride in the apatite containing micro particles in the implanted biomaterial (FIG. 8). At two weeks most of the water soluble set embedding dihydrate sulphate had been resorbed.

Example 6

Size of Apatite Particles in the Binding Mechanism.

Method: We used 25 mg of micro sized pure apatite particles (size: 10 μm) and 25 mg of nano sized apatite particles (size: <200 nm) and placed them bilaterally in the abdominal muscle pouch of rats. Each animal then received a systemic dose of $^{14}$C-ZA 2-weeks post implantation (Injection dose: 0.1 mg/kg ZA, drug/rat: 40 μg, specific radioactivity: 7.1 MBq/mL, ZA concentration: 1 mg/mL). The rats were sacrificed 1-day post injection and the radioactivity in micro and nano apatite particles was measured using scintillation counting.

Results: The uptake of $^{14}$C-ZA was higher in micro-apatite particles compared to nano-apatite particles in 4 out of 5 specimens (FIG. 9).

The experiment indicates that micro sized apatite particles are a better recruiting moiety for $^{14}$C-ZA when compared to nano sized apatite particles.

Example 7

Re-Loading of the Material

Methods: We used 25 mg of micro sized pure apatite particles (size: 10 μm) and 25 mg of nano sized apatite particles (size: <200 nm) and placed them bilaterally in the abdominal muscle pouch of rats. Two different time points were used. At time point 1 (day 14), all animals received the same amount of the radioactive $^{14}$C-ZA. At time point 2 (day 27), half of the animals were given another shot of the drug while the remaining did not. All animals were sacrificed a day later and the uptake of the drug measured in the apatite particles of two different sizes using scintillation counting.

Results: Radioactivity was measured in both the groups and we found that the activity increased in the group that was injected again compared to the group that received only one injection (FIG. 10). This indicates a possibility of reloading these particles with a drug of choice if the need persists. On an average, the nano-apatite particles in the group that received 2 injections had 77% higher counts of $^{14}$C-ZA compared to the animals injected once. Similarly, the micro-particles had an average increase of 72%.

It also show that the nanoparticles at a later stage may allow penetration comparable to microparticles.

Example 8

Nano-Apatite Particles can Penetrate into Common Osteosarcoma Cells.

Methods: MG-63 (a common osteosarcoma cell line) cells were seeded on 96-wells plate at a density of 8000 cells/well. Nano apatite particles or nano apatite particles coupled with ZA were given to the cells at a concentration of 100 μg/mL. Nano particle coupling was performed by suspending apatite particles in PBS followed by addition of ZA to PBS. The particles and the drug were incubated together for 2 h followed by centrifuging the particles and washing them with PBS 2×. The supernatants were discarded and the particles fed to MG-63 cells. At t=day 1, 4 and 7, the viability of the cells was measured using the MTT assay.

Results:

At day 1, no significant differences between nHA or nHA+ZA were seen. At t=day 4 and day 7, nHA+ZA induced cell death in 60% and 90% cells respectively. Only nHA particles induced cell death in approximately 5-10% MG-63 cells (FIG. 11).

Nano apatite particles will pass through the cell wall. By adding a known chemically binding antibiotic like Rifamipicin (in the test nanoparticles was used) or a cytostatic like Doxorubicin (also with nano particles) or zoledronic acid (ZA, which also induces apoptosis in tumor cells), the particles can be taken up by the cells, which should induce apoptosis as shown in FIG. 11.

They could then be loaded and reloaded with the same or a different drug with a binding to the defined sites of HA i.e. Ca,P,OH.

The antibiotic has shown a clear intracellular killing effect. This is extremely important as bacteria in bone lives in the cells like osteoclast, osteoblast or osteocytes (FIG. 16).

This goes for the cytostatic as well both with particles alone but even more in the combination with tumor drugs like ZA or doxorubicin.

Likewise, even microparticles, which we have shown to have a better effect on binding, could exert an effect when being chewed/eaten up by the osteoclast or other giant cell capable of digesting apatite. The immediate killing effect and the reloading will benefit from the different sizes.

Example 9

Vancomycin and Gentamycin Do Not Bind to Apatite.

Not all antibiotics bind to apatite. As a consequence of which a burst release of these antibiotics is seen during the first week period with maximum concentration reached within the first 48 h, also shown in FIG. 12.

The long term studies showed complete release of Gentamycin at one month following the degradation of the soluble sulphate in the biphasic HA/Sulphate carrier (FIG. 13).

Example 10

In-Vitro Test Conducted for the Antibiotic Isoniazid Release from CaS/HA Material.

Method: Isoniazid was mixed to CaS/HA biomaterial and equal volume pellets were created. Each pellet was then placed in a 1.5 mL tube and filled with 1 mL phosphate buffered saline (PBS). At each time point, the old PBS was removed and frozen until the day of analysis. The tube was refilled with fresh PBS (1 mL). All samples were analyzed spectrophotometrically and the concentration of the released antibiotic was calculated from a standard curve of isoniazid made in PBS. The results from in-vitro Isoniazid release experiment are shown in FIG. 14. Results: As seen from FIG. 14, approximately 60% of the antibiotic was already released on day 1 of the experiment indicating that the also the antibiotic Isoniazid lacks affinity for apatite particles.

Example 11

Antibiotics Used in Gram Positive Bone Infection and in Tuberculosis.

Method: Rifampicin was mixed to CaS/HA biomaterial and equal volume pellets were created. Each pellet was then placed in a 1.5 mL tube and filled with 1 mL phosphate buffered saline (PBS). At each time point, the old PBS was removed and frozen until the day of analysis. The tube was refilled with fresh PBS (1 mL). All samples were analyzed spectrophotometrically and the concentration of the released antibiotic was calculated from a standard curve of rifampicin made in PBS. The results from in-vitro rifampicin release experiment are shown in FIG. 15. Results: A sustained release of rifampicin from the CaS/HA biomaterial was observed over a 12-week period with 60% of rifampicin still bound to the CaS/HA biomaterial. At 12-weeks, there is no CaS left in the biomaterial and these findings clearly indicate that the remaining rifampicin in the CaS/HA biomaterial is bound to apatite.

The antibiotic studies taken together indicate that only specific antibiotics interact with apatite and thus the release is slow and these antibiotics administered systemically, seek apatite particles in the body and bind to them.

Example 12

Cytostatics have Affinity for Particulate Apatite

Methods: 5 mg, 10 mg and 20 mg apatite particles were suspended in 1 mL PBS containing 10 μg Doxorubicin and homogenously distributed in the suspension using sonication for 5 min. The specimens were rotated gently on a rotational shaker for 48 h (speed: 50 rpm). After 48 h, the specimens were centrifuged to obtain a pellet of the apatite particles and the supernatant was collected. The apatite particles were then resuspended in 1 mL of PBS, thoroughly pipetted to wash the unbound drug. At this point, the particles were centrifuged again and the supernatant was collected. The washing was repeated once again using the same protocol and the supernatant from the original time and 2 supernatants from the washing steps were measured for fluorescence on a spectro fluorimeter (excitation: 485 nm and emission: 580 nm). Bound doxorubicin to the apatite particles was also detected using fluorescence microscopy. Unbound free drug was used as a control. FIG. 18 shows the results from the in-vitro doxorubicin binding experiment (Spectrophotometrically). FIG. 19 shows the fluorescent microscopy images showing Doxorubicin is actually bound to the apatite particles Results: The amount of HA particles played a major role for the binding. The specimens containing 5 mg apatite particles could bind approximately 10% of the drug. Specimens containing 10 mg apatite particles could bind 30% of the drug and the specimens containing 20 mg particles bound approximately 75% of the drug. This experiment indicates that doxorubicin has a strong concentration dependent affinity to apatite particles.

Example 13

In-Vitro Doxorubicin Release Experiment.

Methods: Pellets of CaS/HA biomaterial were made by mixing 10 μg Doxorubicin/pellet. Each pellet containing 10 μg Doxorubicin was immersed in 1 mL PBS at two different pH (5 and 7.4). At each time point, old PBS was frozen until further analysis and the tube refilled with 1 mL fresh PBS. The experiment was conducted for a period of 4-weeks. Supernatants were analyzed on a spectro fluorimeter (excitation: 485 nm and emission: 580 nm).

Results:

A burst release of approximately 20-35% of the drug was seen from the CaS/HA biomaterial on day 1 and 3 with slightly higher release in the low pH group. No further release of doxorubicin was seen at later time points (FIG. 20).

Example 14

In-Vivo Doxorubicin Binding Experiment.

Methods: 25 mg of nano sized apatite particles (size<200 nm) were implanted in the abdominal muscle pouch of rats. Animals were injected with 5 mg/kg doxorubicin re-suspended in PBS 2-weeks post implantation and the animals were sacrificed 1 day later. The specimens were harvested from the implanted muscle pouch and as a positive control, the site of doxorubicin systemic injection (skin under the neck) was also taken for histology. The samples were embedded in paraffin and cut to a thickness of 5 μm. The samples were then analyzed on a fluorescent microscope (excitation: 485 nm and emission: 580 nm).

Results: Strong fluorescent staining could be observed at the site of injection and relatively weak but positive signal was seen also in the apatite particles and the area immediately around the particles. Muscle taken from 1 cm distal from the implant apatite particles did not show any fluorescence. The results are shown in FIG. 21.

From the experiments above, it appears that the binding is dependent on the chemical structure of the agent being delivered systemically (more free hydroxyl groups on the side chain indicates more binding (FIG. 22), the size and the quantity of the material that is being sought (for instance apatite particles).

Example 15

Improving Fracture Fixation

It's has been shown clinically that it is possible to use the biphasic material in patients undergoing major hip surgery (ref) augmenting a fracture with good long term outcome.

https://www.ncbi.nlm.nih.gov/pubmed/30903873 https://www.ncbi.nlm.nih.gov/pubmed/30522476

Finite element studies have also shown that it is possible to enhance the immediate strength depending on where the material is injected (FIG. 24), incorporated herein by reference in its entirety.

The inventors of present invention have developed a novel method for a material to be injected through a cannulated screw without using a high-pressure injection device (FIG. 25). Simply leaving the screw at a distance from the end of drilled canal and fill the gap trough a cannulated screw with the material according to the invention using a needle or a plastic catheter and then advance the screw thereby pressing out the material to the surrounding bone. This could be combined with adding the apatite material also at the fracture site.

This set up was tested in human femoral heads removed at surgery and showed already initially and an increased pull out strength.

Methods: Human osteoporotic femoral heads removed at the time of hip arthroplasty were reamed to create a cavity in the femoral neck canal. The reaming was stopped approximately 0.5-1 cm before the joint surface. The cannulated screw was then inserted into the canal but stopped approximately 1.5 cm before the end of the canal depth. One specimen received only the cannulated screw, which was then screwed all the way to the depth of the canal. The other specimen received the cannulated screw also stopped approximately 1 cm prior to the end of the canal. At this point, CaS/HA material was injected using a needle, which was placed at the tip of the cannulated screw and 1.5 cc of the material was injected in remaining space of the reamed canal. The HA particles are in range of 1-10 μm. The screw was then tightened such that the material was pushed into the threads of the screw. These specimens were then fixed in a plastic cup and filled with Woods metal to provide support for mechanical testing. After the Woods metal set, the specimens were mounted on a mechanical analyser (Instron® 8511.20 biaxial mechanical analyser) and pulled out at a rate of 0.5 mm/s until failure. The set-up is shown in FIG. 26. The force and displacement curve were used to calculate the peak force required to pull-out the screw in the two groups.

Results: The peak force used to pull-out the screw in the specimen receiving only cannulated screw was approximately 1019 N. The peak force to pull-out the strength in the specimen receiving the cannulated screw and CaS/HA material was approximately 1789 N.

The results indicate that the injection of CaS/HA biomaterial in a cannulated screw can already at the initial surgery enhance mechanical anchorage of the screw to the surrounding bone in this ex-vivo test. Of course, biological remodelling and bone growth around the CaS/HA biomaterial in a living patient will further enhance the anchorage. Screw loosening or proximal penetration is estimated to be 5% of the total cases leading to reoperation with increased mortality. In these scenarios, if the site is already containing millions of apatite particles, systemically administered drugs like ZA can seek and bind to the apatite particles and promote further bone formation and prevent resorption. Another reason for failure is infection and by targeted delivery of apatite seeking antibiotics, it can also be possible to reduce initial biofilm production and even eradicate infection especially in synergistic combination with an non-binding antibiotic delivered locally in high concentrations by degradation of the sulphate component.

Based on the results from the rat study (chamber) we can with high certainty say that we can increase the bone anchorage by giving a systemic injection with a bisphosphonate in the experiment 1.

A pre-set or prefabricated micro particulate material preferably as a rod of different diameter and length could be inserted in a cannulated screw and adjusted according to the length of the canal (FIG. 27).

The screw may have a hole in the front but also be fenestrated on the sides.

Improving Device Anchorage and Local Bacterial Adherence by Coating

Possibility of adding apatite particles on the surfaces to materials of specific size and amount can attract different apatite seeking systemic drugs based on the specific affinity of the drug to the binding sites The material coated with apatite can be initially loaded by soaking in a drug with known chemical affinity and then eventually re-loaded via a systemic injection. This can be used for bone regeneration purposes or killing bugs that attach to the material surface.

Further Applications

Tumour Treatment and Applications

1. We have incorporated one or more agents that binds specifically to apatite and releases over time. An additional drug can be loaded in the sulphate phase with low affinity to apatite which will then be released over a period of time up to 6 months. The material could be preset, fabricated, injectable or moldable
2. We can have none of the cytostatic in the apatite and we can load it with a systemic administration of the drug or eventually re-load it. It could also be radioemitters with broad range of energy spectrum and short and long range cell/tissue penetration.
3. The radioactive tracers or drugs with no apatite binding capacity can be bound chemically to another drug that has a high affinity for apatite. E.g. Zoledronic acid labelled with a cytostatic can be loaded and reloaded.
4. This could be achieved by implanting the material with or without cytostatics from the beginning at different soft and hard tissues and the drug could be reloaded into the material by systemically administering the drug. This would be beneficial for tissues that have low drug uptake.

Bone Implants Containing Interior the Apatite Moiety

1. In one embodiment, we have a fenestrated implant that could be made of a metal or a polymer and the implant is then filled or prefilled with a ceramic material with particulate apatite containing eventually one or more active substances. This would allow for reciprocal diffusion of additional systemic agents to the material which could be beneficial for bone regeneration, implant integration, prevention of infection etc.
2. In one embodiment, for achieving spinal fusion or replacing vertebral bodies, an open cage could be use eventually in combination with external fixation. This cage could by a mini invasive procedure be filled with an injectable apatite material containing active substance like antibiotics, bone active agents and in addition, it could be chemotactically seeked by systemically given drugs (FIG. 28).

Example 16

Practical Illustration with Infection and Bone Defect Illustrating the Apatite Seeking Principle.

A clinical case is presented where a biphasic HA/Sulphate containing antibiotics with Vancomycin and Gentamycin (nonbinding to apatite) is being applied after local debridement and intermediate treatment with a PMMA spacer in a large bone defect (>18 cm). The bone was severely actively infected with pus. The patient had unsuccessfully been operated 5 times earlier for eradication of the infection and bone reconstruction. At 2 week a systemically apatite seeking antibiotic Rifampicin is given and one apatite seeking bone regenerating agent Zoledronic acid is given. The initial release of the Sulphate bound antibiotics have occurred during the first week enriching the local environment with Calcium that chemotactically attracts the apatite seeking agent given systemically. The binding is to micro particulate apatite hydroxyl groups. The patient was infection free post $2^{nd}$ stage of the operation and showed signs of bone union at the distal lateral location already at 2.5 months (FIG. 29)

What is claimed is:

1. A method of treating a subject in need thereof with one or more first pharmaceutically active compounds at a site of the subject, the method comprising the steps of:

i) administering to the site of the subject in need thereof a finely divided (particulate) material, wherein the finely divided material comprises a first material and a second material, wherein the first material comprises hydroxyapatite and consists of a mixture of micro-sized particles in a size range of about 10 μm, and nano-sized particles in a size range of about 40 nm to about 100 nm, wherein the ratio of micro-sized particles and nano-sized particles in the first materials is 1:1, wherein the second material is calcium sulphate hemihydrate and/or di-hydrate;

ii) allowing a period of time to pass in order to provide for a sufficient amount of the second material to be bioresorbed such that the first material is exposed to the body; and iii) systemically administering the one or more first pharmaceutically active compounds after the period of time in (ii), such that the one or more first pharmaceutically active compounds bind to the first material at the site of the subject, wherein the one or more first pharmaceutically active compounds is a bisphosphonate selected from the group consisting of zoledronic acid, etidronic acid, clodronic acid, tiludronic acid, pamidronic acid, neridronic acid, olpadronic acid, alendronic acid, ibandronic acid, risendronic acid and a salt thereof.

2. The method according to claim 1, wherein the calcium sulphate hemi-hydrate and/or di-hydrate is absorbed by the body of the subject within 6 weeks.

3. The method according to claim 1, wherein the second material is pre-loaded or soaked with one or more second pharmaceutically active compounds; wherein the one or more second pharmaceutically active compounds is selected from the group consisting of an antibiotic compound and a bisphosphonate.

4. The method according to claim 3, wherein the one or more second pharmaceutically active compounds display lower affinity for the first material than to the second material.

5. The method according to claim 1, wherein the one or more first pharmaceutically active compounds display lower affinity for the second material than to the first material.

6. The method according to claim 1, wherein a ratio between the first and the second material is in a range of 1% to 99.9%.

7. The method according to claim 6, wherein a ratio between the first and the second material is in a range of 40% to 60%.

8. The method according to claim 1, wherein the first material is additionally pre-loaded or soaked with one or more first pharmaceutically active compounds.

9. The method according to claim 3, wherein the one or more second pharmaceutically active compounds is an antibiotic selected from the group consisting of geldanamycin, herbimycin A, macbecin, natalamycin, streptovaricin, rifamycin, daptomycin, and derivatives thereof.

10. The method according to claim 3, wherein the one or more second pharmaceutically active compounds is a bisphosphonate selected from the group consisting of zoledronic acid, etidronic acid, clodronic acid, tiludronic acid, pamidronic acid, neridronic acid, olpadronic acid, alendronic acid, ibandronic acid, risendronic acid and a salt thereof.

11. The method according to claim 10, wherein the bisphosphonate is a salt including a radioactive compound selected from the group consisting of $^{99}$Tc, $^{223}$Ra, strontium, and samarium, or the bisphosphonate is a compound comprising $^{18}$F.

* * * * *